United States Patent
Spaete et al.

(10) Patent No.: US 6,458,364 B1
(45) Date of Patent: *Oct. 1, 2002

(54) NON-SPLICING VARIANTS OF GP350/220

(75) Inventors: Richard Spaete, Belmont; Winthrop T. Jackman, Berkeley, both of CA (US)

(73) Assignee: Aviron, Burlingame, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/556,706

(22) Filed: Apr. 24, 2000

Related U.S. Application Data

(63) Continuation of application No. 08/783,774, filed on Jan. 15, 1997, now Pat. No. 6,054,130, which is a continuation of application No. 08/229,291, filed on Apr. 18, 1994, now abandoned.

(51) Int. Cl.$^7$ .......................... A61K 39/245; C12N 15/09
(52) U.S. Cl. ................. 424/230.1; 435/69.3; 424/186.1
(58) Field of Search ............................... 435/69.3, 69.1; 424/186.1, 230.1

(56) References Cited

U.S. PATENT DOCUMENTS

| | | |
|---|---|---|
| 4,707,358 A | 11/1987 | Kieff et al. |
| 5,824,508 A | 10/1998 | Spaete et al. |
| 6,054,130 A | 4/2000 | Spaete et al. |

FOREIGN PATENT DOCUMENTS

| | | |
|---|---|---|
| EP | 0 151079 A | 8/1985 |
| EP | 0 312164 A | 4/1989 |
| EP | 0 173 254 | 4/1991 |
| WO | 93 19092 A | 9/1993 |

OTHER PUBLICATIONS

Nemerow et al., 1987, "Identification of gp350 as the Viral Glycoprotein Mediating Attachment of Epstein–Barr Virus (EBV) to the EBV/C3d Receptor of B Cells: Sequence Homology of gp350 and C3 Complement Fragment C3d", J. Virol. 61:1416–1420.

Miller et al., 1972, "Epstein–Barr Virus: Transformation, Cytopathic Changes, and Viral Antigens in Squirrel Monkey and Marmoset Leukocytes", Proc. Natl. Acad. Sci. USA 69 : 383–387.

Whang et al., 1987, "Expression of the Epstein–Barr Virus gp350/220 Gene in Rodent and Primate Cells", J. Virol. 61 : 1796–1807.

Motz et al., 1986, "Expression of the Epstein–Barr Virus Major Membrane Proteins in Chinese Hamster Ovary Cells", Gene 44:353–359.

Emini et al., 1988, "Antigenic Analysis of the Epstein–Barr Virus Major Membrane Antigen (gp350/220) Epressed in Yeast and Mammalian Cells: Implications for the Development of a Subunit Vaccine", Virology 166:387–393.

Madej et al., 1992, "Purification and Characterization of Epstein–Barr Virus gp350/220 Produced by a Bovine Papilloma Virus Expression Vector System", Vaccine 10:777–781.

Finerty et al., 1992, "Protective Immunization Against Epstein–Barr Virus–Induced Disease in Cottontop Tamarins Using the Virus Envelope Glycoprotein gp340 Produced from a Bovine Papillomavirus Expression Vector", J. Gen. Virol. 73:449–453.

David et al., 1988, "Efficient Purification of Epstein–Barr Virus Membrane Antigen gp340 by Fast Protein Liquid Chromatography", J. Immunol. Meth. 108:231–236.

Morgan et al., 1988, "Recombinant Vaccinia Virus Expressing Epstein–Barr Virus Glycoprotein gp340 Protects Cottontop Tamarins Against EB Virus–Induced Malignant Lymphomas", J. Med. Virol. 25:189–195.

Mackett et al., 1985, "Recombinant Vaccinia Virus Induces Neutralising Antibodies in Rabbits Against Epstein–Barr Virus Membrane Antigen gp340", EMBO J. 4 :3229–3234.

Mackett et al., 1986, "Characterization of Vaccinia Virus Recombinants Expressing the Epstein–Barr Virus Membrane Antigen gp340", Vaccines 86 (Cold Spring Harbor Laboratory) pp. 293–297.

Treisman et al., 1981, "Transformation of Rat Cells by an Altered Polyoma Virus Genome Expressing Only the Middle–T Protein", Nature 292:595–600.

Ryu et al., 1989, "Simian Virus 40 Late Transcripts Lacking Excisable Intervening Sequences are Defective in Both Stability in the Nucleus and Transport to the Cytoplasm", J. Virol. 63 :4386–4394.

Gruss et al., 1980, "Rescue of a Splicing Defective Mutant by Insertion of an Heterologous Intron", Nature 286 :634–637.

Straus et al., 1993, "Epstein–Barr Virus Infections: Biology, Pathogenesis, and Management", Ann. Int. Med. 188 : 45–58.

Baer et al., 1984, "DNA Sequence and Expression of the B95–8 Epstein–Barr Virus Genome", Nature 310:207–211.

Beisel et al., 1985, "Two Major Outer Envelope Glycoproteins of Epstein–Barr Virus are Encoded by the Same Gene", J. Virol. 54:665–674.

(List continued on next page.)

*Primary Examiner*—Mary E. Mosher
(74) *Attorney, Agent, or Firm*—Pennie & Edmonds LLP

(57) ABSTRACT

Compositions comprising gp350 variant DNA and amino acid sequences are provided, as are vectors and host cells containing such sequences. Also provided is a process for producing homogeneous gp350 protein recombinantly and in the absence of production of gp220 protein, pharmaceutical compositions containing such protein and prophylactic treatments making use of such proteins.

10 Claims, 7 Drawing Sheets

OTHER PUBLICATIONS

Biggin et al., 1984, "Transcription and DNA Sequence of the BamHI L Fragment of B95–8 Epstein–Barr Virus", EMBO J. 3:1083–1090.

Lees et al., 1993, "The Epstein–Barr Virus Candidate Vaccine Antigen gp340/220 is Highly Conserved Between Virus Types A and B"Virology 195:578–586.

Thorley et al., 1980, "Monoclonal Antibodies Against the Major Glycoprotein (gp350/220) of Epstein–Barr Virus Neutralize Infectivity", Proc. Natl. Acad. Sci. USA 77:5307–5311.

Mount, 1982, "A Catalog of Splice Junction Sequences", Nucl. Acids Res. 10:459–472.

Tartaglia et al., 1990, "Poxvirus–Based Vectors as Vaccine Candidates", Crit. Rev. Immunol. 10;13–30.

Manservigi et al., 1990, "Protection from Herpes Simplex Virus Type 1 Lethal and Latent Infections by Secreted Recombinant Glycoprotein B Constitutively Expressed in Human Cells with a BK Virus Episomal Vector", J. Virol. 64:431–436.

Rose and Bergmann, 1982, "Expression from Cloned cDNA of Cell–Surface Secreted Forms of the Glycoprotein of Vesicular Stomatitis Virus in Eucaryotic Cells", Cell 30:753–762.

Gething and Sambrook, 1982, "Construction of Influenza Haemagglutinin Genes that Code for Intracellular and Secreted Froms of the Protein", Nature 300:598–603.

Spaete et al., 1991, "CMV (Towne) Glycoprotein H (gH) is Complexed with GRP78 and GRP94", in: *Progress in Cytomegalovirus Research*, M.P. Landini, ed., Elsevier Science Publishers, B.V., pp. 133–136.

Spaete et al., 1993, "Coexpression of Truncated Human Cytomegalovirus gH with the UL 115 Gene Product or the Truncated Human Fibroblast Growth Factor Receptor Results in Transport of gH to the Cell Surface", Virology 193:853–861.

Pachl et al., 1989, "The Human Cytomegalovirus Strain Towne Glycoprotein H Gene Encodes Glycoprotein p86", Virology 169:418–426.

Spaete et al., 1990, "Sequence Requirements for Proteolytic Processing of Glycoprotein B of Human Cytomegalovirus Strain Towne", J. Virol. 64:2922–2931.

Spaete et al., 1990, "Human Cytomegalovirus Strain Towne Glycoprotein B is Processed by Proteolytic Cleavage", Virology 167:207–225.

Spaete, 1991, "A Recombinant Subunit Vaccine Approach to HCMV Vaccine Development", Transplant. Proc. 23:90–96.

Pachl et al., "Expression and Characterization of Recombinant Forms of CMV (Towne) Glycoprotein H (gH)", Abstracts of papers presented at the 15th International Herpesvirus Workshop, (Georgetown Univ.) p. 244.

Tosoni–Pittoni et al., 1989, "Complete Characterization of the Gene Coding for the Epstein–Barr Virus Major Membrane Antigen gp 220/340 and Selective Expression of a Secreted Form fo gp 220", Biochem. Biophys. Res. Comm. 158:676–684.

Randle et al. 1985 "Large Scale Purification of EBV Membrane Antigen gp–340 with a Monoclonal Antibody Immunoabsorbent"Journal of Immunological Methods 77:25–36.

Wallace et al. 1991 "Identification of two T–cell epitopes on the Candidate EBV vaccine glycoprotein gp340 recognized by CD4–positive T–cell clones". Journal of Virology 65:3821–3828.

Complaint for Misappropriation of Trade Secrets; Unfair Competition; Breach of Contract, filed, Jul. 1, 1996.

```
3781  CCTGCTGCGGCCCCATGAAGACCACAACTGTGGACCTAGGCCTCTATGCCCCCACCCGAGGGTCATGGGCTCATGCTGTGGGGCAGCACCTCCGTCCGGTCACGTCTCATGTTGGCAT
3901  CATCGATCCCGGCTACACGGGGCAACTCCGGCTAATCCTCCAGAATCAGCGGGCCCTACAACTCCACGCGCTGCGTCCATCGGAGCTCAAAATCCACCTGGCTGCCTTCAGATATGCCACCCC
4021  CCAGATGGAGGAGGACAAGGGTCCCATCAACCACCCCAGTACCCCGGGACGTGGGCCTGGACCTGGCCCTCTTCCCCCATCAGACCGTCTCAGTGACACT
4141  CACCGTGCCCCCCCCTTCTATCCCTCACCACAGCCGACAATCTTTGGCCAGGTCGGGCCCATGGCCTTGCGCATGCACCGTTATTCTAGTGAAGGACCACCACCTCAGTGGGTGGGGTGGGTGGACGTCAG
4261  CCTGACCAACTTTAGTGACCAGACCGTGTTCCTTAACAAGTACCGGCTTTCTGTCAGCTTGTTTACCTTCACAAGCACCACCTCACCTCCTTCTACAGCCCCCACAGCCCCCAGGGT
4381  CCTTGGCCCCCAGATCTCTCTTTAGGTGGGCCAGCTGCACCTTCGAGGAGGTGCCGAGCTGCCATGGGTGATAGTGGGCTGAGGGAGGGAGACAGGGAGGGGTTGG
4501  ATCCTCGGGTCAATGACACCTTCATATCCCTTGTTTTACCAATAAAAATGTTTATTTGGTGTGGAGTCTGGTTGCTACGTTAACGGCAGCTCCTGGGCCCAGAGTGCTCCCGGCTGCCGCA
4621  CCACGGGAGGGCGTGCAAGGACGGGGTGGCACGCCGTGGCCCACCTTCTCCATCTGCCACCTTCTCCATCAGGGCCAGGCTGTCGCCAGCCTGAGGGGCGGTCACCGATGAGACAACGCCCAGATCTCTTGCCCC
4741  AGGCACCGGTCTCGTCCATCTGAGCGCGTATTCCAGATGAGCCCACGGGCCCACGGGCCTGAGCCCATTCGTCCATCTGGATGC
4861  CGCTTACAGGCCAGAGAGATCATGGTATTCCAGATGAGCTGAGCGCACGGGCCCACGGGCCTGAGCCCATTCGTCCATCTGGATGC
```

NON-SPLICING VARIANTS OF GP350/220

This is a continuation of application Ser. No. 08/783,774, filed Jan. 15, 1997 now U.S. Pat. No. 6,054,130; which is a continuation of application Ser. No. 08/229,291, filed Apr. 18, 1994, now abandoned.

TECHNICAL FIELD

This invention relates to methods for making and using and compositions containing Epstein Barr virus (EBV) gp350 DNA and protein sequences.

BACKGROUND

Epstein-Barr virus (EBV), a member of the herpesvirus group, causes infectious mononucleosis in humans. The disease affects more than 90% of the population. Health analysts estimate the cost of the disease in the United States is 100 million dollars per year. The virus is spread primarily by exchange of saliva from individuals who shed the virus. Children infected with EBV are largely asymptomatic or have very mild symptoms, while adolescents and adults who become infected develop typical infectious mononucleosis, characterized by fever, pharyngitis, and adenopathy. People who have been infected maintain anti-EBV antibodies for the remainder of their lives, and are thus immune to further infection. Currently there is no commercially available EBV vaccine.

In addition to its infectious qualities, EBV has been shown to transform lymphocytes into rapidly dividing cells and has therefore been implicated in several different lymphomas, including Burkitt's lymphoma and oral hairy leukoplakia. EBV has also been detected in tissue samples from nasopharyngeal tumors. Worldwide it is estimated that 80,000 cases of nasopharyngeal cancer occur and it is more prevalent in ethnic Chinese populations.

Development of a live, attenuated vaccine for EBV has been and still is problematic. Because of the potential oncogenic nature associated with EBV, researchers have been reluctant to use a live vaccine approach. This invention overcomes the problems associated with live vaccine development by creating methods and compositions for a subunit vaccine, that does not require the use of a potentially oncogenic live virus. A subunit vaccine uses one or more antigenic proteins from the virus that will elicit an immune response and confer immunity.

Two of the more important antigenic EBV proteins are glycoprotein(s) gp350/300 and gp220/200 that form part of the viral membrane envelope and allow virus particles to bind to and enter human target cells by interacting with the cellular membrane protein, CD21. See Nemerow, *J. Virology* 61:1416(1987). They have long been singled out as subunit vaccine candidates but difficulties in obtaining antigenically active protein purified from native sources and low yields from recombinantly produced sources have hampered efforts of researcher and vaccine developers. In the literature these proteins are referred to using a variety of molecular weight ranges (350 or 300 kilodaltons (kD) for one of the proteins and 220 or 200 kDs for the other protein). The gp350 or 300 protein is herein referred to as gp350 protein and the gp220 or 200 protein is herein referred to as gp220 protein. Collectively, both proteins are herein referred to as gp350/220 protein(s).

An alternatively spliced, single gene encodes the gp350/220 proteins and results in the generation of gp350 and gp220 mRNA transcripts; no naturally occurring variations in the gp350/220 gene splice sites are known. The gene produces two expression products, the gp350 and gp220 proteins. The open reading frame for the gp350/220 DNA sequence is 2721 base pairs (bp). The entire reading frame encodes the 907 amino acids of gp350. See U.S. Pat. No. 4,707,358 issued to Kieff (1987). The spliced version of the reading frame covers 2130 bases and translates into gp220 protein, a 710 amino acid sequence. The theoretical molecular weights of gp350 protein and gp220 protein are 95 kD and 70 kD, respectively. The measured molecular weights of expressed gp350 protein and gp220 protein vary but are approximately 350 kilodaltons and 220 kilodaltons (kD), respectively. The extensive glycosylation of the proteins accounts for difference between the predicted and actual molecular weights. In any one cell, both gp350 and gp220 proteins are produced at a molar ratio ranging from about 6:1 to 1:1. For example, in B95-8 cells, which are persistently infected with EBV, the ratio appears to vary but sometimes approaches the 6:1 range. See, Miller, *Proc. Natl. Acad. Sci.* 69:383(1972).

Similarly, recombinant production of these glycoproteins has heretofore usually resulted in a mixture of gp350 and gp220 protein being produced. Heretodate, the gp350/220 proteins have been expressed in rat pituitary, Chinese hamster ovary VERO (African green monkey kidney) cells, as well as in yeast cells. See, Whang, *J. Virol.* 61:1796(1982), Motz, *Gene* 44:353(1986) and Emini, *Virology* 166:387 (1988). A bovine papillomavirus virus expression system has also been used to make gp350/220 proteins in mouse fibroblast cells. See, Madej, *Vaccine* 10:777(1992). Laboratory and vaccine strains of Vaccinia virus have also been used to express gp 350/220 proteins. Modified recombinant versions of the EBV gp350/220 DNA and protein are known in the art. Specifically, recombinant truncated constructs of the gp350/220 gene lacking the membrane spanning sequence have been made. Such constructs still produce a mixture of the two gp 350 and gp220, but deletion of the membrane spanning region permits secretion of the proteins. See, Finerty, *J. Gen. Virology* 73:449(1992) and Madej, *Vaccine* 10:777(1992). Also, various recombinantly produced restriction fragments and fusion proteins comprising various gp350/220 sequences have also been made and expressed in *E. coli*. See EP Patent Publication 0 173 254 published Jul. 24, 1991.

Accordingly, EBV research relating to gp350/220 heretodate has focused either on obtaining efficient expression of the native gp350/220 sequence or on a modified sequence lacking the transmembrane domain, resulting in a mixture of the two alternate spliced versions of the native or transmembrane lacking protein, or on production of epitopic fragment sequences in β-galactosidase fusion proteins.

Partially purified preparations of gp350/220 are known. See, Finerty, *J. Gen. Virology* 73:449(1992) (recombinantly produced, partially purified). With respect to native gp350/220 protein, in most instances, the purification procedures resulted in inactivating the antigenicity of the protein, making it unacceptable for use in a subunit vaccine. However, highly purified preparations of antigenically active gp350 protein from native (i.e., non-recombinant) sources have been reported in the scientific literature. See, David, *J. Immunol. Methods* 108:231(1988). Additionally recombinant vaccine virus expressing gp350/220 protein was used to vaccinate cottontop tamarins against EBV-induced lymphoma. See, Morgan, *J. Med. Virology* 25:189(1988), Mackett, *EMBO J.* 4:3229(1985) and Mackett, *VACCINES '86*, pp293(Lerner R A, Chanock R M, Brown F Eds., 1986, Cold Spring Harbor Laboratory). However, the viral gp350/220 DNA sequence has not heretofore been engineered so as to enable expression solely of either one of the alternate spliced versions of the gene, thereby enabling and ensuring the production of pure gp350 or gp220 protein. Nor has a recombinant or mutant virus been made that expresses one or the other of the gp350 or gp220 proteins.

Generally, splice sites facilitate the processing of pre-mRNA molecules into mRNA. In polyoma virus, splice sites are required for the efficient accumulation of late mRNA's. Alteration of the 3' and 5' splice sites in polyoma virus transcripts decreased or completely blocked mRNA accumulation. See, Treisman, *Nature* 292:595(1981). In SV40 virus, excisable intervening sequences facilitate mRNA transport out of the nucleus and mRNA stabilization in the nucleus and because these intron/exon junction sequences facilitate binding of small, nuclear, RNP particles, it is thought that prespliced mRNA's might fail to associate properly with processing pathways. It has been shown that point mutations at exon/intron splice sites reduce exon/intron cleavage and can disrupt pre-mRNA processing, nuclear transport and stability. See, Ryu, *J. Virology* 63:4386 (1989) and Gross, *Nature* 286:634(1980).

Therefore, until the present invention, the effect of splice site modification on the functional expression and antigenic activity of the proteins encoded by the EBV gp350/220 sequence was at best unknown and unpredictable.

Additional background literature includes the following. EBV biology and disease is generally reviewed in Straus, *Annal of Int. Med.* 118:45(1993). A description of the EBV BLLFI open reading frame is found in Baer, *Nature* 310:207 (1984). Descriptions of the Epstein-Barr virus gp350/220 DNA and amino acid sequences are found in articles by Beisel, *J. Virology* 54:665(1985) and Biggin, *EMBO J.* 3:1083(1984) and in U.S. Pat. No. 4,707,358 issued to Kieff, et al. (1987). A comparison of DNA sequences encoding gp350/220 in Epstein-Barr virus types A and B is disclosed in Lees, *Virology* 195:578(1993). Monoclonal antibodies that exhibit neutralizing activity against gp350/220 glycoprotein of EBV are disclosed in Thorley-Lawson, *Proc. Natl. Acad. Sci.* 77:5307(1980). Lastly, splice site consensus sequences for donor and acceptor splice sites are disclosed in Mount, *Nucleic Acids Res.* 10:459(1982).

SUMMARY OF THE INVENTION

In one aspect this invention provides non-splicing variants of the EBV gp350/220 DNA sequence. The DNA sequences of the invention may include an isolated DNA sequence that encodes the expression of homogeneous gp350 protein. The DNA sequence coding for gp350 protein is characterized as comprising the same or substantially the same nucleotide sequence in FIG. 1 wherein the native nucleotides at the donor and acceptor splice sites are replaced with non-native nucleotides, and fragments thereof. This DNA sequence may include 5' and 3' non-coding sequences flanking the coding sequence and further include an amino terminal signal sequence. FIG. 1 illustrates the non-coding sequences and indicates the end of the putative signal sequence with an asterisk. It is understood, however, that the DNA sequences of this invention may exclude some or all of these flanking or signal sequences. The non-splicing variant DNA sequences of the invention are produced by introducing mutations into the FIG. 1 DNA sequence in the donor and acceptor splice sites of the gene encoding gp350/220. This eliminates production of gp220 protein so that only the gp350 protein is produced.

Accordingly, in another aspect the invention comprises homogeneous gp350 proteins, and methods of making the proteins by expression of the non-splicing variant of EBV gp350/220 DNA sequence in an appropriate prokaryotic or eukaryotic host cell under the control of suitable expression control sequence. As the term is used here with respect to gp350 proteins, homogeneous means free or substantially free from gp220 protein. We note that homogeneous gp350 protein, recombinantly produced in mammalian or insect cells, has not to our knowledge ever been reported in the scientific literature heretofore.

In yet another aspect, homogeneous gp350 proteins, additionally having deletions resulting in a secreted product are provided. Such deletions comprise either removal of the transmembrane region or removal of the transmembrane region and the remaining C-terminus of gp350. Such additionally modified DNA sequences and the proteins encoded thereby are yet another aspect of this invention.

Also provided is a recombinant DNA molecule comprising vector DNA and a DNA sequence encoding homogeneous gp350 protein. The DNA molecule provides the gp350 sequence in operative association with a suitable regulatory sequence capable of directing the replication and expression of homogeneous gp350 in a selected host cell. Host cells transformed with such DNA molecules for use in expressing recombinant homogeneous gp350 are also provided by this invention.

The DNA molecules and transformed host cells of the invention are employed in another aspect of the invention, a novel process for producing recombinant homogeneous gp350 protein or fragments thereof. In this process a cell line transformed with a DNA sequence encoding a homogeneous gp350 protein or fragment thereof (or a recombinant DNA molecule as described above) in operative association with a suitable regulatory or expression control sequence capable of controlling expression of the protein is cultured under appropriate conditions permitting expression of the recombinant DNA. The expressed protein is then harvested from the host cell or culture medium by suitable conventional means. The process may employ a number of known cells as host cells; presently preferred are mammalian cells and insect cells.

The DNA sequences and proteins of the present invention are useful in the production of therapeutic and immunogenic compounds having EBV antigenic determinants. Such compounds find use in subunit vaccines for the prophylactic treatment and prevention of EBV related diseases, such as mononucleosis, Burkitt's lymphoma and nasopharyngeal carcinoma. Accordingly, in yet another aspect the invention comprises such therapeutic and/or immunogenic pharmaceutical compositions for preventing and treating EBV related conditions and diseases in humans such as infectious mononucleosis, Burkett's lymphoma and nasopharyngeal carcinoma. Such therapeutic and/or immunogenic pharmaceutical compositions comprise a immunogenically inducing effective amount of one or more of the homogeneous gp350 proteins of the present invention in admixture with a pharmaceutically acceptable carrier such as aluminum hydroxide, saline and phosphate buffered saline as are known in the art. By "immunogenically inducing" we mean an amount sufficient for stimulating in a mammal the production of antibodies to EBV. Alternatively, the active ingredient may be administered in the form of a liposome-containing aggregate. For prophylactic use, such pharmaceutical compositions may be formulated as subunit vaccines for administration in human patients. Patients may be vaccinated with a dose sufficient to stimulate antibody formation in the patient; and revaccinated after six months or one year.

A further aspect of the invention therefore is a method of treating EBV related diseases and conditions by administering to a patient, particularly to a human patient, an immunogenically inducing therapeutically effective amount of a homogeneous gp350 protein in a suitable pharmaceutical carrier. Still another aspect of the invention is a method of stimulating an immune response against EBV by administering to a patient an immunogenically inducing effective amount of a homogeneous gp350 protein in a suitable pharmaceutical vehicle.

Other aspects and advantages of the invention are described further in the following detailed description.

DESCRIPTION OF THE FIGURES

FIGS. 1A–1D illustrates the DNA and amino acid sequence of gp350/220 (From Beisel, *J. Virology* 54:665 (1985)). The donor and acceptor splice sites are indicated. The transmembrane region is delineated with the horizontal arrows and an asterisk (*) marks the end of the putative signal sequence. Nucleotide numbering is shown at the left; amino acid numbering at the right.

DETAILED DESCRIPTION

Figure 2A:
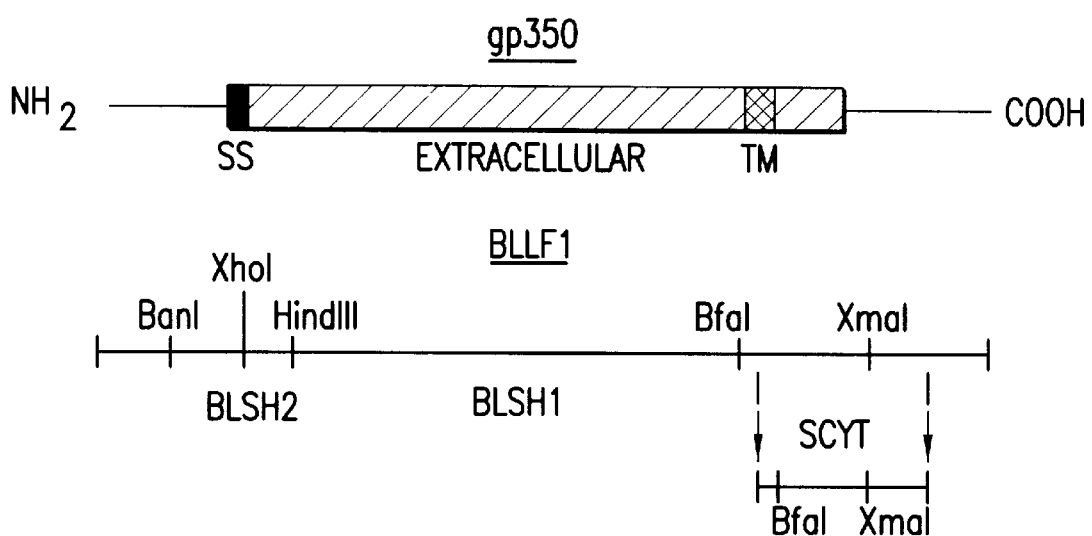
FIGS. 2A–2B illustrates construction of gp350 deletion and site directed mutants. The plasmid maps labelled pMDTM and pMSTOP exemplify the non-splicing gp350/220 variants of the invention. In section (A), a linear model of the gp350 protein is shown approximately to scale with the encoding clone, BLLF1, below. An N-terminal signal sequence (SS) and the transmembrane domains (TM) are indicated on the protein and important restriction sites are indicated on the gene diagram. The gp350 gene was cloned in two segments, the HindIII/BfaI BLSH1 fragment and the BanI/HindIII BLSH2 fragment. SCYT was created using the polymerase chain reaction from the region of BLLF1 indicated. In (B), the cloning scheme for pDTM, pSTOP, pMDTM, and pMSTOP is illustrated (plasmids not to scale). The details of the cloning are described in Examples 1 and 2. Plasmid maps are marked with the relevant restriction sites, the cloning vectors used and the gp350 gene fragments. Splice site mutations in pMDTM and pMSTOP are indicated by asterisks.

Disclosed are compositions and methods comprising cloned EBV DNA sequences encoding non-splicing variants of gp350 protein. As noted, such non-splicing variants are referred to herein as homogeneous gp350 proteins. Normally, when the gp350/220 gene is expressed in mammalian cells two gene products are generated, gp350 and gp220, due to RNA splicing of the gene. The invention allows for only one gene product, gp350, to be produced. The invention involves removing some or all of the RNA splice site signals in the gp350 gene and expressing the gene in a suitable host cell. Mutations in the gp350/220 gene were introduced to prevent production of the 220 kD version of the protein when the gp350/220 gene is expressed in mammalian cells. As a result, mRNA transcripts encoding only gp350 are produced. The elimination of gp220 expression by using a gp350/220 gene non-splicing variant will result in increased production of gp350 relative to gp220. Production of gp220 is not essential for production of an effective anti-EBV vaccine because gp350 contains all the potential antigenic sites found on gp220.

Therefore, one aspect of this invention provides a DNA sequence encoding a polypeptide sequence substantially the same as gp350, except that the donor splice site codon encoding amino acid 501 and the acceptor splice site codon encoding amino acid 698 have been modified by replacement of native nucleotides with non-native nucleotides. Preferably the native nucleotides are replaced with non-native nucleotides such that the amino acid sequence remains the same. Specifically, in the example, native nucleotides AAGT at the donor splice site (nucleotides 1500 through 1504) and native nucleotides A and T flanking the GG acceptor splice site (nucleotides 2091 and 2094) were replaced with nucleotides GTCA and T and A, respectively. Consequently, the Glutamine at amino acid position 500 and the Serine at position 501 remained the same as a result of this substitution in the donor site. Likewise, the Threonine at amino acid position 697 and the Glycine at position 698 remained the same as a result of the modification in the acceptor site.

Analogously, substitutions other than those specifically exemplified could readily be performed by one skilled in the art as is more fully described below.

Therefore, in one aspect the invention comprises homogeneous gp350 proteins. The homogeneous gp350 proteins are further characterized by having an amino acid sequence substantially the same as that shown in FIG. 1 from amino acids 1 through 907, from amino acids 1 through 862 or from amino acids 1 through 907 and excepting amino acids 863 through 881, each with or without the N-terminal 18 amino acid signal sequence. In addition, analogs of homogeneous gp350 proteins are provided and include mutants in which there are variations in the amino acids sequence that retain antigenic activity and preferably have a homology of at least 80%, more preferably 90%, and most preferably 95%, with the corresponding region of the homogeneous gp350 proteins. Examples include proteins and polypeptides with minor amino acid variations from the amino acid sequence of FIG. 1; in particular, conservative amino acids replacements. Conservative replacements are those that take place within a family of amino acids that are related in their side chains. Genetically encoded amino acids are generally divided into four families. (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan and tyrosine are sometimes classified jointly as aromatic amino acids. For example, it is reasonable to expect that an isolated replacement of a leucine or a similar conservative replacement of an amino acid with a structurally related amino acid will not have a major effect on antigenic activity or functionality.

The invention offers the advantage of simpler purification of gp350. Because gp350 and gp220 have similar biochemical properties, gp220 is often co-purified in preparations of gp350. Cells expressing only the non-splicing variant of the gp350/220 gene simplifies protein purification. This will reduce the costs of producing gp350. The invention also makes biochemical characterization of the starting material for gp350 purification easier. Because only one species is present, protein content analysis and amino acid sequence analysis may be performed without accounting for the presence of a second species.

The invention additionally offers the advantage of increased gp350 production. Prevention of gp350 gene splicing will shift the cell from dual production of gp350 and gp220 to the production of gp350 alone. In some cells, the concentrations of gp220 have been estimated to be 30%–100% of the gp350 concentration. With the gene splicing eliminated, gp350 production will be increased by the lack of gp220 production.

Figure 1C:
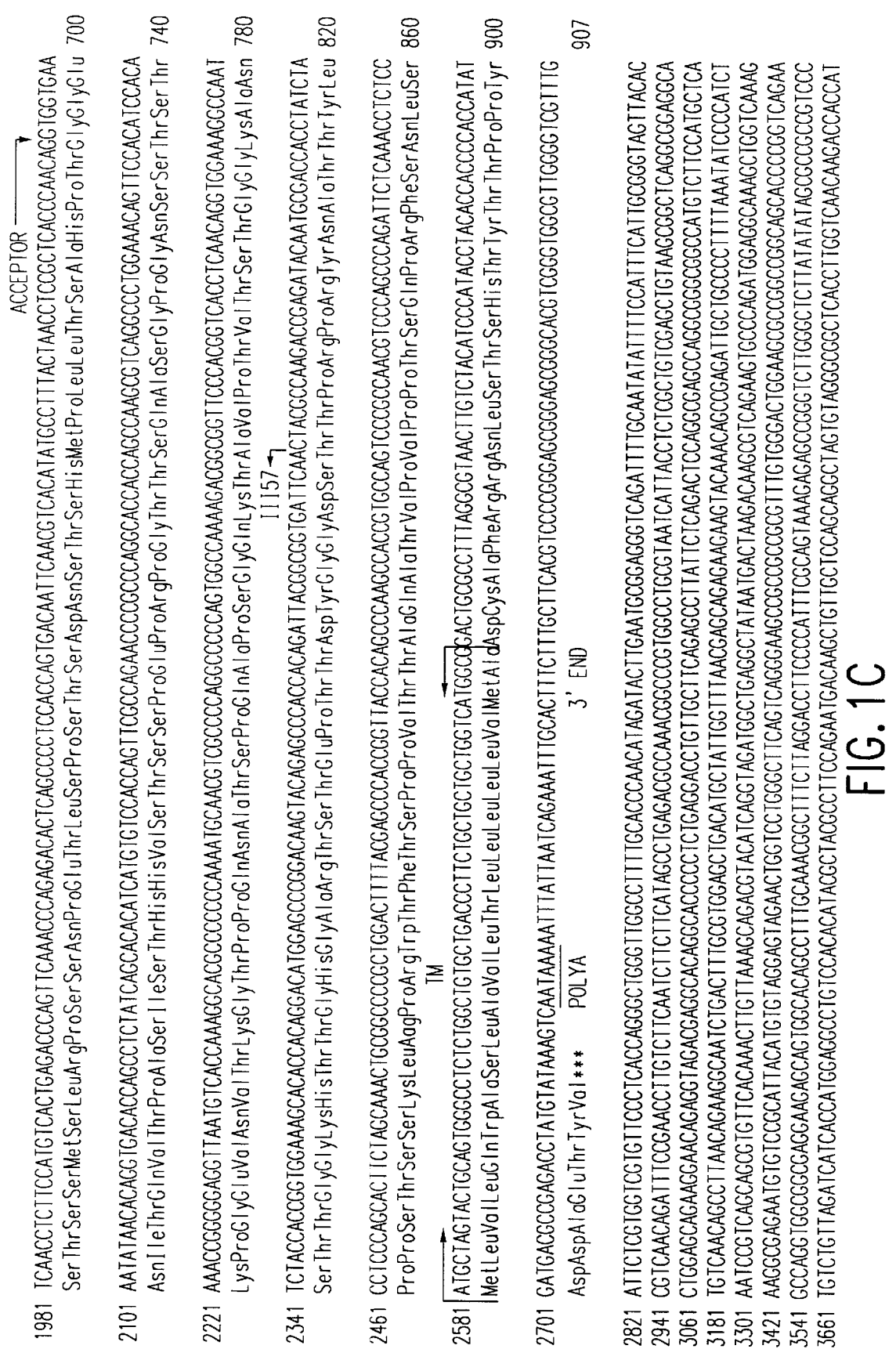

The DNA sequence of the gp350/220 gene is described by Beisel, *J. Virology* 54:665(1985) and Biggin, *EMBO J.* 3:1083(1984) and is illustrated in FIG. 1. The gene is an open reading frame of 2721 bases, encoding 907 amino acids and specifying a primary translation product of about 95 kD. The difference between predicted and actual values represents extensive glycosylation of the protein. 591 bases (encoding 197 amino acids) are spliced out to produce gp220. The apparent molecular weight of gp350/220 gene products may also vary depending upon the type of measurement system used, glycosylation site utilization in different cell types, post-translational processing differences or selective gene mutation. Measured values vary for the products of different gp350/220 gene non-splice site variants but the term "homogeneous gp350 protein or proteins" encompasses gene products of the non-splicing variant, optionally having additional deletions or mutations such as the C-terminal deletions and/or transmembrane modifications also disclosed herein. The term "gp220 protein" refers to the alternatively spliced gp350/220 gene product with a molecular weight of approximately 220 kD. Splice-sites in the gp350/220 gene were identified by comparison of the gp350/220 gene with consensus donor and acceptor splice sequences based on other genes, predominantly from eukaryotic organisms. The consensus sequences developed by Mount, *Nucleic Acids Res.* 10:459(1982) from studying the splice sites in other genes are:

Donor: A/C AG/G*T*A/G AGT

Acceptor: T/C $N_{11}$C/TA*G*/G

The bases asterisked above represent bases that appear in 100% of all splice sites (highly conserved). Positions with two bases or one base represent conserved positions (non highlighted positions). The slash indicates the actual site of splicing.

In the gp350/220 gene the donor splice site occurs after nucleotide 1501 and the acceptor splice occurs after nucleotide 2092, as shown by DNA sequencing (Biggin. *EMBO J.* 3:1083(1984)) of the gp350/220 gene. (The numbering used herein and in FIG. 1 conforms to the numbering in Biggin). The splice site occurs in the corresponding gene region in the Type B strain of EBV (the donor splice site after $A_{1501}$ and the acceptor splice site after $G_{2202 9}$). The invention encompasses compositions made using either the A or B strain or another EBV strain's splice site to produce a single species of mRNA from the gp350/220 gene. The DNA sequence of the Type A form of the virus from strain B95-8 was used in the Examples although the DNA sequence of the Type B strain could equally have been used, because the translated gene products of Type A and B strains are 98% identical. The B strain lacks amino acids 507 through 520 and 570 through 576. The type A strain was used because it contains all the possible gp350 antigenic sites. Alternatively, EBV gp350/220 having strain-specific sequences could be used in accordance with the teachings herein to produce EBV strain-specific homogeneous gp350 proteins having immunogenic properties specific to a particular strain and therefore useful in immunogenic and/or therapeutic compositions for the prevention or treatment of strain specific EBV related diseases. Table 1 shows the wild type nucleotide and amino acid sequences of the donor and acceptor splice sites.

To prevent RNA splicing of the gp350/220 gene, mutations were introduced into the gp350/220 gene nucleic acid sequence to replace the relevant base pairs of the RNA splice site. To render a splice-site nonfunctional, preferably at least one of the bases out of the two highly conserved bases framing the donor site or acceptor site should be replaced with nonconserved bases, more preferably at least two highly conserved bases should be mutated to nonconserved bases. Other conserved bases, more than two bases away from the splice site, can also be replaced with nonconserved splice site bases to further decrease recognition of the splice site. Both the donor and the acceptor site can be changed to impair splicing mechanisms. Preferably, both the donor and the acceptor contain at least one change each, in one of the four highly conserved splice site base positions, and more preferably at least two changes in two of the four highly conserved splice site base positions. If one splice site is not mutable due to a desire to maintain the wild-type amino acid sequence then it is preferable to introduce at least two mutations to the other splice site.

Mutation at the gp350/220 splice sites may introduce changes into the amino acid sequence of the subsequently expressed gp350 protein. Preferably such changes should be conservative amino acid substitutions. Conservative substitutions in the amino acid sequence, as opposed to nonconservative changes in the amino acid sequence, will help preserve antigenic sites. Conservative amino acid changes can be made as long as the base change (or base changes) result in a suitable change in the invariant donor/acceptor bases. For example, Gly could be substituted for $Ser_{501}$ at the donor splice site, using any Gly-specific codons other than GGU (use of GGU would preserve the G nucleotide and would not result in the desired GT replacement in the splice signal). Likewise, at the acceptor splice site, $Gly_{698}$ to Ala would be a conservative change, but since all Ala codons start with the highly conserved G nucleotide, this would not result in the desired replacement. Although Proline also might be a conservative amino acid change, proline would not be used to replace a wild type amino acid because it would result in modification of the tertiary structure of the protein and thereby mask one or more gp350 antigenic sites. Table 1 shows the acceptable conservative amino acid replacements in the wild-type sequences. At the bottom of Table 1 is an example of a mutation with conservative amino acid changes.

TABLE 1

| Donor | | | Acceptor | |
|---|---|---|---|---|
| Wild-type Sequences | | | | |
| GAA | splice A \| GT | ACA | splice G \| GT | |
| Glu | $Ser_{501}$ | Thr | $Gly_{698}$ | |
| ↓ | ↓ | ↓ | ↓ | |
| | Conservative a.a. changes | | | |
| Asn | Ala | Ala | Ser | |

TABLE 1-continued

|     | Donor |     | Acceptor |     |
|-----|-------|-----|----------|-----|
|     | Asp   | Gly | Gly      | Thr |
|     | Gln   | Thr | Ser      |     |
| ex.:| GAC   | ACA | TCG      | TCT |
|     | Asp   | $Thr_{501}$ | Ser | $Ser_{698}$ |

Although one aspect of the present invention comprises a non-splicing variant of gp350/220, additional mutations of the gp350/220 coding sequence may also be desirable. In order to produce soluble homogeneous gp350 proteins ("soluble proteins" are either free in solution or membrane associated but are not membrane integrated), for example, to avoid cell toxicity problems incurred by the expression of full length gp350 as an integral membrane protein, the membrane spanning region (also known as the transmembrane region) of gp350 is modified by deletion of all or part of its encoding DNA sequence. The membrane spanning region of gp350/220 comprises amino acids 861 (methionine) through 881 (alanine). See, Beisel, *J. Virology* 54:665(1985). Preferably, at least 8 amino acids of the transmembrane region are deleted, more preferably at least 12 amino acids are deleted and most preferably between 18 and 21 amino acids are deleted. Accordingly, in another aspect, the invention provides non-splicing variants of gp350/220 DNA and/or gp350 homogeneous protein additionally comprising at least one deletion in the transmembrane region of the gp350/220 DNA and/or gp350 homogeneous protein that results in the expression of soluble homogeneous gp350 protein.

In addition to deleting all or part of the transmembrane domain of the non-splicing gp350/220 variant, the C-terminal sequence following the transmembrane domain and comprising amino acids 881 through 907 may also be deleted in whole or in part, as described herein, in accordance with the invention. Thus, in another aspect the invention comprises non-splicing variants of gp350/220 DNA and/or homogeneous protein further modified by deletion of all or a portion of the DNA encoding and/or amino acid sequence comprising the transmembrane region of gp350/220 and even further modified by deletion of the remaining C-terminal DNA and/or amino acid sequences of gp350/220.

Accordingly, in another aspect the invention comprises non-splicing variant DNA sequences encoding the homogeneous gp350 proteins of the invention. Such DNA sequences comprise the DNA sequence of FIG. 1 encoding amino acids 1 through 907 and further comprising the nucleotide substitutions taught herein to remove the donor and acceptor splice sites. Such DNA sequences optionally comprise truncated DNA sequences in which the nucleotides encoding all or part of the transmembrane domain and C-terminus comprising amino acids 861 through 907 are deleted and deletion variants in which the nucleotides encoding all or part of the transmembrane domain comprising amino acids 861 through 881 are deleted. The DNA sequences of the present invention encoding homogeneous gp350 proteins may also comprise DNA capable of hybridizing under appropriate stringency conditions, or which would be capable of hybridizing under such conditions but for the degeneracy of the genetic code, to an isolated DNA sequence of FIG. 1. Accordingly, the DNA sequences of this invention may contain modifications in the non-coding sequences, signal sequences or coding sequences, based on allelic variation, species variation or deliberate modification.

These non-splicing variant gp350/220 DNA sequences as disclosed herein can be constructed using methods well known in the art. The modified DNA sequences of this invention can be expressed recombinantly, likewise using known methods, to produce the homogeneous gp350 proteins of this invention. Such recombinant proteins can be purified and incorporated into pharmaceutical compositions for the prophylactic treatment and prevention of EBV related diseases.

The non-splicing variants of gp350/220 DNA of this invention can be expressed recombinantly in different types of cells using the appropriate expression control systems as is known in the art. Suitable cells known and available in the art include, but are not limited to, yeast cells such as *Saccharomyces cerevisiae*, bacterial cells such as *E. coli* and *Bacillus subtilis* and mammalian cells such as GH3, CHO, NSO, MDCK and C-127 cells. Vectors used with cell types are selected based on their compatibility with the cell type and expression control system used. Cells and vectors that allow for the expression of secreted products of the gp350/220 gene are preferred. Typically for example, *E. coli* is transformed using derivatives of pBR322 which have been modified using conventional techniques to contain the DNA sequences for expression of the desired protein, in this instance the non-splicing variant sequences of EBV gp350, with or without the sequences encoding the C-terminus and/or membrane spanning region. pBR322 contains genes for ampicillin and tetracycline resistance, which can be used as markers. See, Bolivar, *Gene* 2:95(1977). Commonly used expression control sequences, i.e., promoters for transcription initiation and optionally an operator or enhancer, include the beta-lactamase and lac promoter systems (see Chang, *Nature* 198:1056(1977)), the tryptophan promoter system (see Goeddel, *Nucleic Acids Res.* 8:4057(1980)) and the lambda-derived PL promoter and N-gene ribosome binding site (see Shimatake, *Nature* 292:128(1981). However, any available promoter system or expression control system that is compatible with prokaryotic host cells can be used. Other exemplary host cells, plasmid and expression vehicles are disclosed in U.S. Pat. No. 4,356,270 issued to Itakura (1982), U.S. Pat. No. 4,431,739 issued to Riggs (1984) and U.S. Pat. No. 4,440,859 issued to Rutter (1984).

Insect cells may also be used as host cells employing insect cell expression. In the case of expression in insect cells, generally the components of the expression system include a transfer vector, usually a bacterial plasmid, which contains both a fragment of the baculovirus genome, and a convenient restriction site for insertion of the heterologous gene or genes to be expressed; a wild type baculovirus with a sequence homologous to the baculovirus-specific fragment in the transfer vector (this allows for the homologous recombination of the heterologous gene in to the baculovirus genome); and appropriate insect host cells and growth media.

Currently, the most commonly used transfer vector for introducing foreign genes into AcNPV is pAc373. Many other vectors, known to those of skill in the art, have also been designed. These include, for example, pVL985 (which alters the polyhedrin start codon from ATG to ATT, and which introduces a BamHI cloning site 32 basepairs downstream from the ATT; see Luckow and Summers, *Virology* (1989) 17:31.

The plasmid usually also contains the polyhedrin polyadenylation signal (Miller et al. (1988) *Ann. Rev. Microbiol.*, 42:177) and a procaryotic ampicillin-resistance (amp) gene and origin of replication for selection and propagation in *E. coli*.

Baculovirus transfer vectors usually contain a baculovirus promoter. A baculovirus promoter is any DNA sequence capable of binding a baculovirus RNA polymerase and initiating the downstream (5' to 3') transcription of a coding sequence (e.g. structural gene) into mRNA. A promoter will have a transcription initiation region which is usually placed proximal to the 5' end of the coding sequence. This transcription initiation region typically includes an RNA polymerase binding site and a transcription initiation site. A baculovirus transfer vector can also have a second domain called an enhancer, which, if present, is usually distal to the structural gene. Expression can be either regulated or constitutive. For insect cell expression technology, see EP patent publication 155 476.

Yeast, for example *Saccharomyces cervisiae*, may also be used as a host cell. Various strains are available and may be used. Likewise, plasmid vectors suitable for yeast expression are known, as are promoter and expression control systems. See for example, Myanohara, *Proc. natl. Acad. Sci.* 80:1(1983)(PHO5 promoter), EP Patent Publication 012 873 (leader sequences), Kurtz, *Mol. Cell. Biol.* 6:142(1986), Ito, *J. Bacteriol.* 153:163(1983) and Hinnen, *Proc. Natl. Acad. Sci.* 75: 1929(1979)(transformation procedures and suitable vectors).

Eukaryotic cells from multicellular organisms may of course also be used as hosts cells for the expression of genes encoding proteins and polypeptides of interest. Useful host cell lines include VERO and HeLa cells, and Chinese hamster ovary cells (CHO). Expression vectors compatible with such cells are also available and typically include promoters and expression control sequences, such as for example, the early and late promoters from SV40 (see Fiers, *Nature* 273:113(1978)) and promoters from polyoma virus, adenovirus 2, bovine papilloma virus or avian sarcoma virus. Exemplary host cells, promoters, selectable markers and techniques are also disclosed in U.S. Pat. No. 5,122,469 issued to Mather (1992), U.S. Pat. No. 4,399,216 issued to Axel (1983), U.S. Pat. No. 4,634,665 issued to Axel (1987), U.S. Pat. No. 4,713,339 issued to Levinson (1987), U.S. Pat. No. 4,656,134 issued to Ringold (1987), U.S. Pat. No. 4,822,736 issued to Kellems (1989) and U.S. Pat. No. 4,874,702 issued to Fiers (1989).

Transformation of suitable host cells is accomplished using standard techniques appropriate to such cells, such as $CaCl_2$ treatment for prokaryotes as disclosed in Cohen *Proc. Natl. Acad. Sci.* 69:2110(1972) and $CaPO_4$ precipitation for mammalian cells as disclosed in Graham, *Virology* 52:546 (1978). Yeast transformation can be carried out as described in Hsiao, *Proc. Natl. Acad. Sci.* 76:3829(1979) or as described in Klebe, *Gene* 25:333(1983).

The construction of suitable vectors containing the non-splicing variant gp350 sequence (with or without the additional modifications disclosed here resulting in deletion of the C-terminus and/or the membrane spanning region) is accomplished using conventional ligation and restriction techniques now well known in the art. Site specific DNA cleavage is performed by treating with suitable restriction enzyme(s) under standard conditions, the particulars of which are typically specified by the restriction enzyme manufacturer. Polyacrylamide gel or agarose gel electrophoresis may be performed to size separate the cleaved fragments using standard techniques and the fragments blunt ended by treatment with the Klenow fragment of *E. coli* polymerase I in the presence of the four deoxynucleotide triphosphates. Treatment with S1 nuclease hydrolyzes any single-stranded portions. Synthetic oligonucleotides can be made using for example, the diethylphosphoamidite method known in the art. See U.S. Pat. No. 4,415,732 (1983). Ligations can be performed using T4 DNA ligase under standard conditions and temperatures and correct ligations confirmed by transforming *E. coli* or COS cells with the ligation mixture. Successful transformants are selected by ampicillin, tetracycline or other antibiotic resistance or using other markers as are known in the art.

Such recombinant DNA techniques are fully explained in the literature. See, e.g. Sambrook, MOLECULAR CLONING: A LABORATORY MANUAL, 2D ED. (1989); DNA CLONING, Vol. I and II (D N Glover ed 1985); OLIGONUCLEOTIDE SYNTHESIS (M J Gait ed 1984); NUCLEIC ACID HYBRIDIZATION (B D Hames ed 1984); TRANSCRIPTION AND TRANSLATION (B D Hames ed 1984); ANIMAL CELL CULTURE (R I Freshney ed 1986); B. Perbal, A PRACTICAL GUIDE TO MOLECULAR CLONING (1984); GENE TRANSFER VECTORS FOR MAMMALIAN CELLS (J H Miller ed 1987 Cold Spring Harbor Laboratory); Scopes, PROTEIN PURIFICATION: PRINCIPLES AND PRACTICE, 2nd ed, (1987 Springer-Verlag NY) and HANDBOOK OF EXPERIMENTAL IMMUNOLOGY Vols I–IV (D M Weired 1986). All such publications mentioned herein are incorporated by reference for the substance of what they disclose.

Accordingly in another aspect the invention comprises vectors containing the non-splicing variants of gp350/220 DNA sequences and host cells and further comprises a method of making a non-splicing variant of gp350/220 protein by culturing said host cells containing a vector that is carrying a non-splicing variant of a gp350/220 DNA sequence operatively linked to an expression control sequence under culture conditions enabling expression of the homogeneous gp350 protein.

The expressed homogeneous gp350 is purified from cell and culture medium constituents using conventional glycoprotein purification techniques such as, but not limited to, ultrafiltration, free flow electrophoresis, gel filtration chromatography, affinity chromatography, SDS-PAGE, differential $NH_4SO_4$ precipitation, lectin columns, ion exchange columns and hydrophobicity columns as is known in the art. Small scale analytical preparations of gp350 are most readily purified using SDS-PAGE or lectin affinity columns and such small scale preparations for use in vaccination or immune response experiments are most readily purified using liquid chromatography. For large scale production of commercially significant quantities of gp350 for use in vaccine compositions, a combination of ultrafiltration, gel filtration, ion exchange, and hydrophobic interaction chromatography are preferred.

The purified, homogeneous gp350 proteins of the present invention may be employed in therapeutic and/or immunogenic compositions for preventing and treating EBV related conditions and diseases such as infectitious mononucleosis, Burkitt's lymphoma and nasopharyngeal carcinoma. Such pharmaceutical compositions comprise an immunogenically-inducing effective amount of one or more of the homogeneous gp350 proteins of the present invention in admixture with a pharmaceutically acceptable carrier, for example an adjuvant/antigen presentation system such as alum. Other adjuvant/antigen presentation systems, for instance, MF59 (Chiron Corp.), QS-21 (Cambridge Biotech Corp.), 3-DMPL (3-Deacyl-Monophosphoryl Lipid A) (RibiImmunoChem Research, Inc.), clinical grade incomplete Freund's adjuvant (IFA), fusogenic liposomes, water soluble polymers or Iscoms (Immune stimulating complexes) may also be used. Other exemplary pharmaceutically acceptable carriers or solutions are aluminum hydroxide, saline and phosphate buffered saline. The composition can be systemically administered, preferably subcutaneously or intramuscularly, in the form of an acceptable subcutaneous or intramuscular solution. Also inoculation can be effected by surface scarification or by inoculation of a body cavity. The preparation of such solutions, having due regard to pH, isotonicity, stability and the like is within the skill in the art. The dosage regimen will be determined by the attending physician considering various factors known to modify the action of drugs such as for example, physical condition, body weight, sex, diet, severity of the condition, time of administration and other clinical factors. Exemplary dosage ranges comprise between about 1 μg to about 1000 μg of protein.

In practicing the method of treatment of this invention, an immunologically-inducing effective amount of homogeneous gp350 protein is administered to a human patient in need of therapeutic or prophylactic treatment. An immunologically inducing effective amount of a composition of this invention is contemplated to be in the range of about 1 microgram to about 1 milligram per dose administered. The number of doses administered may vary, depending on the above mentioned factors. The invention is further described in the following examples, which are intended to illustrate the invention without limiting its scope.

EXAMPLE 1

Figure 2B:
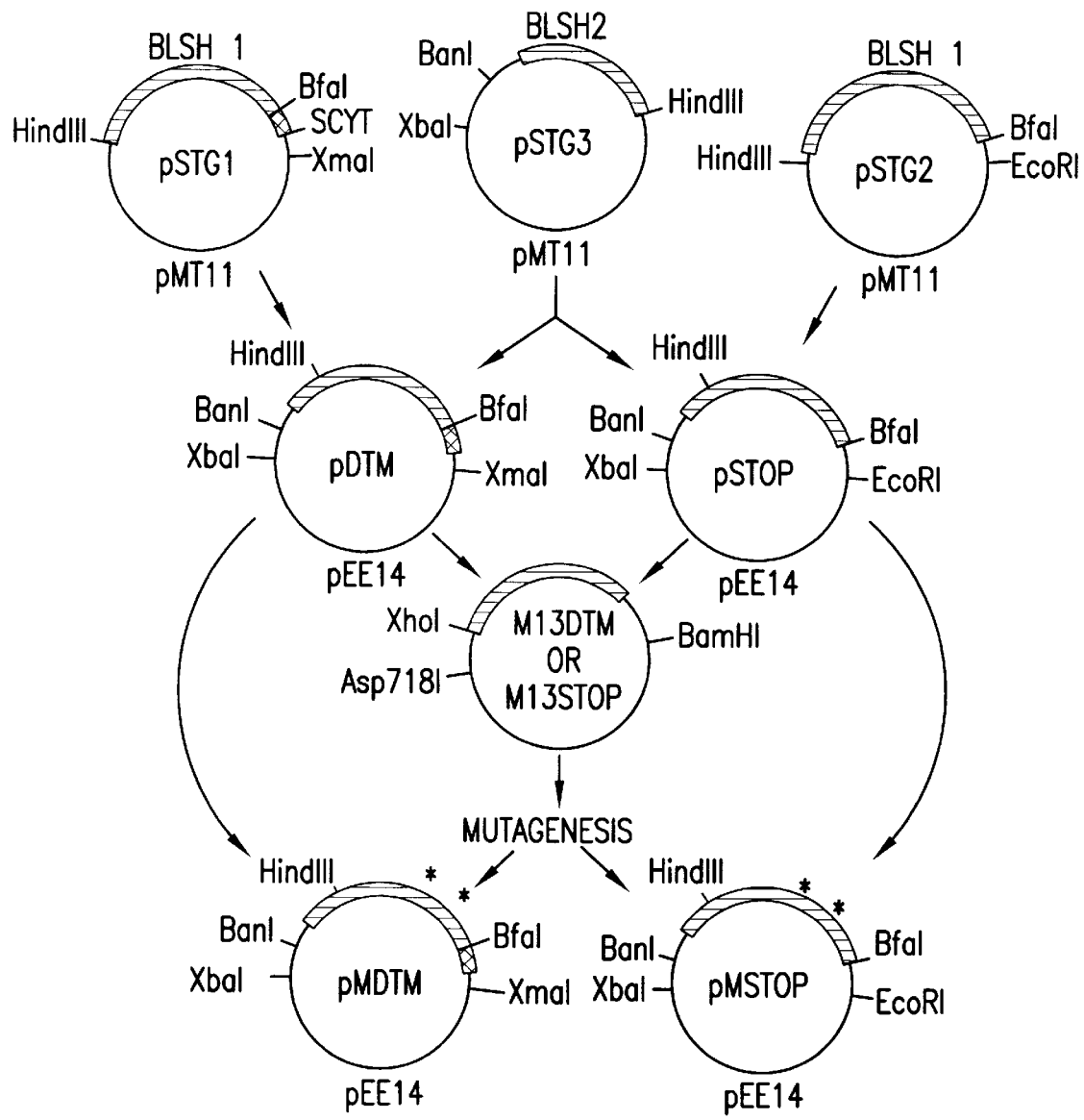

Deletion of the gp350/220 Transmembrane Region and Transmembrane Region through C-terminus to create pDTM and pSTOP The gp350/220 gene from the EBV B95-8 strain (Miller, et al., 1972), is available in a BamHI library as an open reading frame called BLLF1 (Baer, *Nature* 310:207, 1984). To create the desired constructs (shown diagrammatically in FIG. 2B), the gp350/220 gene was cloned in two parts: 1) BLSH1, a 2.3 kb HindIII/BfaI 3' fragment and 2) BLSH2, a 337 b.p. BanI/HindIII 5' fragment (FIG. 2A). These fragments were cloned into staging vectors so that the deletions of the C-terminal cytoplasmic and/or transmembrane-encoding domains could be performed. Because the BfaI site occurs at the 5' end of the region encoding the gp350 transmembrane (TM) domain, it was used to construct the TM domain deletions and TM domain deletions with adjacent C-terminus deletions. Using BfaI, it was possible to create deletions retaining only two amino acids of the TM region (Table 2).

1. Construction of pDTM From pSTG1, and pSTG3

The plasmid pDTM is comprised of a gp350/220 nucleic acid sequence that lacks a complete TM coding region. This construct was made using two staging vectors pSTG1 and pSTG3. A 450 bp PCR product, SYCT, that introduced a BfaI site at the 3' end of the TM region was made using a BLLF1 clone target sequence (FIG. 2). The PCR primers used are as follows:

BfaI

```
                              -continued
Primer 1: GG ATC CTA GAC TGC GCC TTT AGG CGT A
BLLF1:             ... GAC TGC GCC TTT AGG CGT A..
A.A.:              ... Asp Cys Ala Phe Arg Arg ...
                     |__End of TM Region Primer 2: GGA TCC TCT GTT CCT TCT GCT CCA GTG
BLLF1:    ... ...    TCT GTT CCT TCT GCT CCA GTG
```

The BfaI site of Primer 1 was used to clone a BfaI/XmaI fragment of SCYT into pSTG1. The remainder of Primer 1 corresponds to the amino acid sequence encoded by clone BLLF1. Primer 2 corresponds to a region outside the gp350/220 open reading frame on the 3' side of the gene. The SCYT PCR fragment was cut with BfaI and XmaI to produce a 136 base pair fragment which was cloned into a pMT11 vector (Spaete and Mocarski, 1985) along with a second fragment, a BLSH1 HindIII/BfaI fragment, to create pSTG1. Sequencing across the BfaI site indicated that all of the TM amino acid coding region was deleted except for amino acids Met and Leu (see Table 2). A third BLLF1 fragment, BLSH2, was cloned into pMT11 to create pSTG3. A 16 base pair BanI/XbaI oligonucleotide linker outside of the gp350/220 gene coding sequence was used to clone the BLSH2 BanI/HindIII fragment into the pSTG3. A 2.4 HindIII/XmaI pSTG1 fragment, was cloned into a pEE14 vector (Celltech, England) together with a 0.3 XbaI/HindIII pSTG3 fragment to complete the pDTM construct.

2. Construction of pSTOP using Vectors pSTG2 and pSTG3

The plasmid pSTOP comprises a gp350/220 gene that lacks a TM region and the C-terminal cytoplasmic region adjacent the TM region. To create this construct, a 16 base pair BfaI/EcoRI oligonucleotide linker was created with stop codons (underlined) in three frames following the BfaI sticky end as shown below:

TAT AGA CTA GTC TAGG A TCT GAT CAG ATC CTT AA

The 5' overhang (TA) of the upper sequence is a sticky end for a BfaI restriction site and the 5' overhang (TTAA) of the lower sequence is an EcoRI sticky end. This 16 base pair linker was used to clone a BLSH1 HindIII/BfaI fragment into pMT11, in order to create pSTG2. A 2.3 kb pSTG2 HindIII/EcoRI fragment and the pSTG3 0.3 kb XbaI/HindIII fragment were cloned into pEE14 to create pSTOP.

3. Comparison of the Wild-type, pDTM and pSTOP Sequences at the TM Region

The oligonucleotide sequence and translated amino acid sequence of the wild type, pSTOP, and pDTM 3' ends of gp350 DNA and amino acid sequences are shown in Table 2 below. Arrows indicate the beginning and end of the wild-type transmembrane domain (TM). Only two amino acids from the transmembrane domain are retained in pDTM and pSTOP, $Met_{861}$ and $Leu_{862}$ (see also FIG. 1). Note that a stop codon immediately follows $Leu_{862}$ in pSTOP. In pDTM the former location of the deleted transmembrane region is marked "ΔTM". (In the Table, the native amino acids are indicated.)

TABLE 2

```
3' End of gp350 Wild-Type Sequence
...AAC CTC TCC ATG CTA GTA CTG.....GTC ATG GCG GAC TGC GCC
...Asn Leu Ser Met Leu₈₆₂ Val Leu.....Val Met Ala Asp₈₈₂ Cys Ala
             ↑                              ↑
             TM start                       TM end
```

TABLE 2-continued

```
3' End of pSTOP
...AAC CTC TCC ATG CTA TAG ACT AGT TCT AGG ...
...Asn Leu Ser Met Leu862 STOP

3' End of pDTM
...AAC CTC TCC ATG CTA GAC TGC GCC...
...Asn Leu Ser Met Leu862 Asp882 Cys Ala....
                            Λ
                           ΔTM
```

EXAMPLE 2

Removal of the gp3501220 Gene Donor and Acceptor Splice Sites to Create pMDTM and pMSTOP In order to obtain homogeneous production of a gp350 protein the highly conserved and conserved bases of the gp350/220 gene splice site were changed. Four bases were changed in the donor splice site, including the highly conserved GT pair that occurs in 100% of all splice sites. Two conserved donor site bases, AA, were replaced with GT. The two highly conserved (invariant) donor splice site bases were changed from GT to CA. At the acceptor splice site, only one of the highly conserved acceptor splice site bases was altered to preserve the amino acid sequence. A second conserved acceptor splice site base was changed as indicated in Table 3. Table 3 summarizes the bases changed in the donor and acceptor splice sites of the gp350/220 gene.

TABLE 3

EBV gp350/220 Gene Splice Site Changes

```
Donor Splice site:
              donor                  donor
Wild-type:    GAA A↓GT    mutant:    GAG* T*C*A*
              Glu Ser501              Glu Ser501
Acceptor Splice site:
              acceptor               acceptor
Wild-type:    ACA G↓GT    mutant:    ACT* GGA*
              Thr Gly698              Thr Gly698
```

The bases changed by oligonucleotide-based mutagenesis are marked with an asterisk in the mutant sequences. The actual site of splicing is indicated by an arrow, and the encoded amino acids are shown. Note that the amino acid sequence does not change as a result of the nucleotide substitutions.

These nucleotide substitutions to the wild type gp350/220 donor splice site and accepter splice site DNA sequences were accomplished using oligonucleotide-mediated mutagenesis. A modified phage vector, M13TAC, was employed to produce mutations as described in Zoller, M. E. and Smith, M. (1983) *Methods of Enzymol.* 100:468.

BamHI/XhoI fragments of the gp350/220 nucleotide sequence were cloned into the polylinker of plasmid M13TAC using Asp718 and BamHI restriction sites on the polylinker, combined with a 19 bp oligonucleotide Linker containing Asp718 and XhoI sticky ends. The plasmids M13DTM and M13STOP of Example 1 (FIG. 2B), were used for the mutagenesis.

Two 42-mer oligonucleotides, PrDonorl and PrAcceptorl, were made for use in the mutagenesis. Each was designed to be complementary to gp350/220 gene sequences centering on either the donor or acceptor splice sites. The only region of the oligonucleotides that were not complementary to the gp350/220 gene were the bases representing the desired mutations. Mutagenesis oligonucleotides comprised the following:

```
PrDonor1
Primer:    GGT CAT GTC GGG GGC CTT TG |A  CTC TGT GCC GTT GTC CCA TGG
                                   ** |*  *
EBV:       GGT CAT GTC GGG GGC CTT AC |T  TTC TGT GCC GTT GTC CCA TGG PrAcceptor1
Primer:    CTG TGT TAT ATT TTC ACC TC |C  AGT TGG GTG AGC GGA GGT TAG
                                    * |   *
EBV:       CTG TGT TAT ATT TTC ACC AC |C  TGT TGG GTG AGC GGA GGT TAG
```

The sequence of the mutagenesis oligonucleotides are labelled "Primer," while the DNA sequence spanning the gp350/220 gene splice sites are labelled "EBV." Bases that were changed as a result of the mutagenesis are marked with an asterisk. The dashed line indicated the location of the splice.

The oligonucleotides PrDonor1 and PrAcceptor1 were hybridized to single-stranded clones of M13-DTM and M13-STOP. T4 DNA polymerase holoenzyme was used to produce double-stranded M13 DNA and *E. coli* was transformed with the double-stranded DNA. Using the vector M13TAC, any clone that contained the desired mutation could be identified by a color change from white to blue in the presence of X-gal and isothiopropylgalactate. Blue plaques were picked and grown up, and DNA sequencing across splice junctions was used for the final identification of mutant clones, labelled M13-MDTM and M13-MSTOP.

After identifying clones containing the desired mutations, BamHI/XhoI fragments were cut out of M13-MDTM and M13-MSTOP and ligated back into pDTM or pSTOP backbones to create the constructs pMDTM and pMSTOP, respectively. These constructs were transfected into CHO cells to express the non-splicing variant gp3501220 DNA sequences as described in Example 3.

EXAMPLE 3

Expression of gp350 in CHO Cells
1. Transfection of gp350/220 Gene Constructs One method for producing high levels of homogeneous gp350 protein of the invention from mammalian cells involves the construction of cells containing multiple copies of the heterologous gp350 DNA sequence. The heterologous DNA sequence is operatively linked to an amplifiable marker, in this example, the glutamine synthetase gene for which cells can be amplified using methionine sulphoximine.

The pMDTM and pMSTOP vectors made in Example 2 were transfected into CHO cells as discussed below, according to the procedures of Crockett, *Bio/Technology* 8:662 (1990) and as described in the Celltech Instruction Manual for the glutamine synthetase gene amplification system (1992).

CHO-K1 cells (ATCC CCR61) were maintained in glutamine-free EMEM (Eagles Minimal Essential Medium) supplemented with 10% fetal bovine serum, 100 units/ml penicillin, 100 mg/ml streptomycin, MEM (Modified Eagle's Medium) nonessential amino acids, and 1 mM sodium pyruvate (all obtained from JRH Biosciences). The media was also supplemented with 60 mg/ml glutamic acid, 60 mg/ml asparagine, 7 mg/ml adenosine, 7 mg/ml guanosine, 7 mg/ml cytidine, 7 mg/ml uridine, and 2.4 mg/ml thymidine (all from Sigma.) This media preparation was used throughout the transfection, with deviations from this recipe as noted.

One day prior to transfection 10-cm dishes were seeded with $3 \times 10^6$ CHO-K1 cells. On the day of transfection the cells were washed with 10 ml serum-free media per dish. Plasmid DNA (from the pMDTM, pMSTOP plasmids) was applied by $CaPO_4$ precipitation using conventional techniques. 10 μgs of each plasmid DNA precipitate was incubated with the CHO-K1 cells plus 2 ml of serum-free media at 37° C. for 4.5 hours. Three replicates of each of the four plasmid DNA transfections were made. The cells were then shocked for 1.5 minutes with 15% glycerol in HEPES-buffered saline. After rinsing with serum-free media, the cells were re-fed with serum-containing media and incubated for 24 hours.

The following day the media was changed to include 10% dialyzed fetal bovine serum (JRH Biosciences) and amplified by the addition of 25 μM methionine sulphoximine (Sigma). Cells were re-fed with methionine sulphoximine-containing media every 3–5 days until the amplified clones were large enough for picking, approximately 13–14 days later. Clones were picked by scraping colonies off the dish with a sterile 200 μl pipetman tip and transferred to one well of a 96-well plate in media without methionine sulphoximine. 1–2 days later the media was replaced with media+25 μM methionine sulphoximine. After 4 days the culture supernatants were harvested and assayed for protein products in an ELISA assay, as discussed below.

CHO cells were also transfected with the pEE14 control vector alone (which contains no EBV sequences) and 24 clones of CHO-pEE14 were also picked and transferred to plates to serve as controls. (The control clones were identified on the basis of survival in methionine sulphoximine.)

2. ELISA Assay

Following transfection, 241 clones of CHO-pMDTM and 158 clones of CHO-pMSTOP were picked and grown up. Supernatants from these clones were tested for gp350 protein production. 96-well plates were coated with affinity-purified rabbit anti-gp350/220 antibody (antibody MDP1; gift of Andrew Morgan) diluted 1:2000 in 5 mM sodium borate buffer, pH 9. The plates were incubated at 37° C. for 3–4 hours and washed 3 times with PBS+0.05% Tween 20 using a Nunc ImmunoWasher. After blotting dry, the plates were blocked by incubating with 2% BSA in PBS+0.01% Thimerosal at 37° C. for 0.5 hours and washed again. Supernatants from the transfected cells and control cells were added to the wells and incubated for 2 hours at 37° C. The plates were then incubated with the primary detection antibody, a mouse monoclonal antibody against gp350/220 (antibody #C65221M; Biodesign International) at 1 mg/ml diluted in PBS wash buffer, 37° C. for 1 hour. After washing, the plates were incubated with the secondary antibody, horseradish peroxidase-conjugated goat $F(ab)_2$ fragments directed against mouse immunoglobulins (Human Ig adsorbed; Biosource International.), 0.7 μg/ml in PBS+ 0.05% BSA and 0.01% Thimerosal, at 37° C. for 1 hour. The plates were washed and developed using ABTS (Pierce Chemicals) dissolved in Stable Peroxide Substrate Buffer (Pierce Chemicals) for 0.5 hours at room temperature. The reaction was stopped with 1% SDS and the plates were read at 405 and 650 nm wavelengths using a Molecular Devices Vmax ELISA plate reader. 24 pMDTM and 18 pMSTOP clones tested positive for secreted gp350. The clones exhibiting the highest ELISA signal were transferred to 24-well plates for scale-up and further testing in a Western Blot and a radioimmunoprecipitation assay.

3. Western Blot and Radio Immunoprecipitation Assay

In an initial screening, tissue culture supernatants from the pMDTM transfections were assayed for activity in a Western Blot. CHO cell supernatants were purified on 5% SDS-PAGE gels, transferred to nitrocellulose overnight, and probed with anti-gp350 antibodies. Seven pMDTM clones were found to be positive for gp350 in the Western blot analysis.

The pMDTM clones that were positive in the Western blot were further tested by radioimmunoprecipitation for the presence of gp220. Selected transformed pMDTM cells, pEE14 control and GH3Δ19 control cells (described below) were grown overnight in six-well plates so that they were approximately three-quarters confluent on the day of the experiment. Each well contained approximately $5 \times 10^6$ cells. For labelling, the media was removed from each well and replaced with 0.7 ml of methionine-free MEM (10% fetal calf serum)+100 μCi $^{35}$S-methionine. The cells were incubated 5.5 hours at 37° C. and then microcentrifuged at 4000 rpm for 5 minutes. Homogeneous gp350 protein in the supernatant was immunoprecipitated by addition of 10 μl of Sepharose-Protein A (Sigma) in a 50% slurry and 20 μl monoclonal anti-gp350/220 (antibody #C65221M, 100 mg/ml; Biodesign International), with overnight rocking at 4° C. The mixture was then pelleted at 2000 rpm, 2 minutes at room temperature in a microcentrifuge and washed four times with several volumes of phosphate-buffered saline. After the final wash, all liquid was removed from the pellet and replaced with 50 μl protein gel sample buffer. The samples containing the precipitated immuno-complex were boiled 5 minutes and run on a 5% SDS-PAGE. Immunoprecipitates were compared to gel samples of tissue culture supernatants mixed 1:1 with protein sample buffer. The gel was dried and autoradiographed with Hyperfilm β-Max (Amersham).

Figure 3:
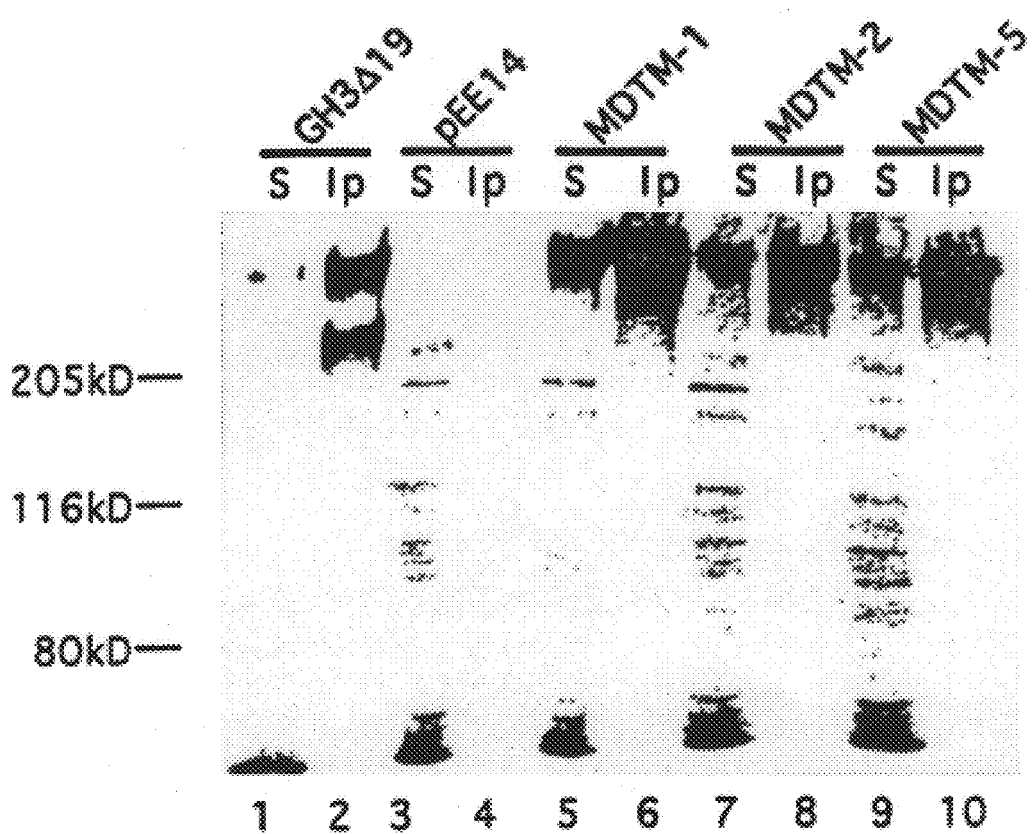
FIG. 3 illustrates the results of immunoprecipitation of homogeneous gp350 protein from pMDTM clones as analyzed by SDS-PAGE. Positive control (GH3Δ19) cells secreting a truncated form of the gp350/220 proteins, negative control (pEE14) cells and several pMDTM clones were metabolically labeled with $^{35}$S-methionine for 5.5 hours; homogeneous gp350 protein was immunoprecipitated from the resulting tissue culture supernatants. For each cell type, samples of labeled tissue culture supernatants (S) and gp350/220 precipitations (Ip) were electrophoresed on 5% SDS-PAGE (polyacrylamide gel electrophoresis). Location of molecular weight markers are indicated on the left side.

FIG. 3 shows the autoradiographic results of SDS-PAGE analysis of the radioimmunoprecipitation. The cell line used as a positive control was GH3Δ19 (gift of Elliot Keiff; Whang et al., 1987). GH3Δ19 cells secrete a truncated form of the gp350/220 protein lacking the transmembrane and C-terminal cytoplasmic domains. For use as a negative control, CHO cells were transfected with the pEE14 vector alone and selected by methionine sulphoximine in parallel with the pMDTM transfection. In FIG. 3, supernatants ("S") are shown in odd numbered lanes, alternated with immunoprecipitates ("Ip") shown in even numbered lanes. In control lane 2, precipitation from the GH3Δ19 control cells results in two strong protein bands at approximately 220 and 350 kD demonstrating production of the truncated splice variant gp350 and gp220 proteins in about a 1:1 ratio. As expected, these immunoprecipitated bands are concentrated with respect to the radiolabelled tissue culture supernatant (non-immunoprecipitated sample) in lane 1. Also, as expected, no bands are shown in the negative control (lane 4), since the pEE14 vector does not contain any of the gp350/220 constructs.

SDS-PAGE analysis of the immunoprecipitation from supernatants of pMDTM clones in lanes 6, 8 and 10 results in a single strong band at approximately 350 kD, the same as the higher molecular weight species in the GH3Δ19 control lane 2. In contrast to the GH3Δ19 control lane however, an additional strong band at approximately 220 kD is absent from lanes 6, 8 and 10, although in lane 8 a very faint band migrating at a slightly lower molecular weight is revealed. This could represent a degradation product, a co-precipitated cellular product or a small amount of gp220 protein resulting from a mistranslation or a mutational event that returns the deleted donor and acceptor splice sites to the native nucleotide or amino acid sequences. Strong single bands at approximately 350 kD were found in five other MTDM replicates tested (data not shown).

It is unlikely that the complete absence of the band at 220 kD in lanes 6 and 10 is due to inefficient precipitation from MDTM supernatants since in the $^-$S-labelled GH3Δ19 control lane (2), a band at 220 kD is easily visualized. Also, additional assays using the pDTM constructs of Example 1 that contain the wild type splice sites result in two strong bands at 350 and 220 kD. Therefore, these results demonstrate that deletion of the splice sites results in production of gp350 protein in the absence of production of gp220 protein.

This homogeneous gp350 protein, expressed in CHO cell lines, or in other mammalian or non-mammalian cell lines, can be further scaled up and homogenous gp350 protein can be isolated and purified from conditioned medium from the cell line using methods familiar in the art, including techniques such as lectin-affinity chromatography, reverse phase HPLC, FPLC, gel filtration and the like. See David, *J. Immunol. Methods* 108:231(1988) and Madej, *Vaccine* 10:777(1992).

EXAMPLE 4

Testing the Homogeneous gp350 Proteins for Immunogenic Activity

The purified homogeneous gp350 proteins are incorporated into appropriate vehicles for administration and administered to mice as follows.

A 2×adjuvant-vehicle concentrate is prepared by mixing Pluronic L121 and squalane in 0.4% (v/v) Tween 80 in phosphate buffered saline with (Thr$^1$) MDP in accordance with the procedure of David, *J. Immunol. Methods* 108:231 (1988) and Allison, *J. Immunol. Methods* 95:157(1986).

The composition for administration is prepared by addition of equal volumes of protein and adjuvant-vehicle on the day of administration. The protein content should be with range of 5 micrograms to 50 micrograms per dose.

BALB/c mice are immunized with three 0.1 ml intramuscular injections at 0.21 and 42 days. A pre-immunization bleed and successive bleeds taken 10 days after each injection are obtained from the retro-orbital sinus.

Serum antibody levels are determined by an ELISA according to the procedures described in Example 3. EBV neutralizing antibodies in the sera are quantified by their ability to inhibit transformation of fetal cord blood lymphocytes by EBV in vitro according to the methods of Moss, *J. Gen. Virol.* 17:233(1972) and De Schryver, *Int. J. Cancer* 13:353(1974).

Alternatively, New Zealand white rabbits are inoculated by intramuscular administration of five doses of protein emulsified in the foregoing adjuvant at 0, 21, 42, 63 and 84 days. The dose should be in the range of about 5 μg to 50 μg per inoculation. Sera is obtained two weeks following the last dose and tested for antibody titers to the antigen, for cross-reactive antibody to viral gp350/220 from B95-8 cells and for in vitro EBV-neutralizing activity following the methods of Emini, *Virology* 166:387(1988).

Because the ability of the EBV gp350/220 protein to induce protective immunity in an animal model of EBV infection has already been established, see Epstein, *Clin. Exp. Immunol* 63:485(1986), similar positive results from administration of a homogeneous gp350 protein composition are expected.

The disclosures of all publication identified herein are expressly incorporated herein by reference. The foregoing detailed description is given for clearness of understanding only and no unnecessary limitations are either understood or inferred therefrom, as modifications within the scope of the invention will be obvious to those skilled in the art.

We claim:

1. A method of producing a gp350 protein for use in pharmaceutical compositions comprising:
   (a) culturing host cells transformed with a DNA sequence encoding EBV gp350 protein having a deletion in the membrane spanning region and the remaining carboxy terminus, and/or a deletion of the signal sequence, said DNA sequence, having a mutation at one or more splice sites preventing formation of a gp220 mRNA transcript; and
   (b) isolating the expressed homogeneous gp350 from the cell and culture medium.

2. The method of claim 1 wherein the homogeneous gp350 is further isolated by ultrafiltration, gel filtration, ion exchange, and hydrophobic interaction chromatography.

3. The method of claim 1 or 2 wherein the homogeneous gp350 is formulated in admixture with a pharmaceutically acceptable carrier.

4. The method of claim 3 wherein the pharmaceutically acceptable carrier is an adjuvant/antigen presentation system.

5. The method of claim 1 wherein said mutation at one or more splice sites is a mutation in the donor splice site.

6. The method of claim 1 wherein said mutation at one or more splice sites is a mutation in the acceptor splice site.

7. The method of claim 5 or 6 in which at least one native nucleotide encoding serine at codon 501 of SEQ. ID. No.: 18 is replaced with a non-native nucleotide, and in which at least one native nucleotide encoding glycine at codon 698 of SEQ. ID. No.: 18 is replaced with a non-native nucleotide.

8. The method of claim 6 wherein the DNA encodes a shortened version of EBV gp350 having a deletion of at least 8 amino acids in the membrane spanning region, resulting in a secreted product.

9. The method of claim 8 wherein said mutation at one or more splice sites is a mutation in the donor splice site.

10. The method of claim 8 wherein said mutation at one or more splice site is a mutation in the acceptor splice site.

* * * * *

SEQUENCE LISTING

<160> NUMBER OF SEQ ID NOS: 19

<210> SEQ ID NO 1
<211> LENGTH: 5931
<212> TYPE: DNA
<213> ORGANISM: Virus
<220> FEATURE:
<223> OTHER INFORMATION: gp350/220

<400> SEQUENCE: 1
gaattccata aatgaaacac gctggtcagg tgttaaaact tcctcccaga ttttcgtgag      60
gctcctgtgt atagccatat agtcaaagaa aatactgtag cggggattac agctctgtac     120

-continued

| | | |
|---|---|---|
| aatgttaccc acggagctct gaacatacaa ccactgcgga tccccggggg tacatcgcgg | 180 | |
| cagcttaaag gtgccggcgg aaaaggtcac gtgacaccta cggccacctg tgcacccaag | 240 | |
| tgtcgcctgg agatgtacga atgtgggagt cgtctggtga tcgtgtagc tgtacatcca | 300 | |
| gctgctgtat gcctggtaac ccataggcca tccggcggcc agggtttgca gtctccattt | 360 | |
| ggcctgatct ctacgagaag ctggatttct ccgacgatct ctaatggcct gtcgaatggc | 420 | |
| catggcatac attatgtaca tctcggtatt tgaaatctgg atccgaaaaa ctggtctatg | 480 | |
| gctcgtgtgt cgatgcgctg aaaccaacgg caacaaatta cttaccttgt tgttgtgtga | 540 | |
| tgggtaaaaa cacacatcac acacttaggc catagggatg ctcaccgtag ccgcggctcc | 600 | |
| aatcgcttga agaagtgttc ttagatctag tggaaacctg cggagaatgg cttctcgccc | 660 | |
| agggagatcc ggctggggtg ggagcatggg tcgtgctgga gctgacccac cggcatcatg | 720 | |
| atcgacccgc tttctcttcg tacccttctg ggccggctcc agtgggcat cttctgcttc | 780 | |
| cttttctgag ctgctatctg ataactctat gaggacattt tcccaatctc ccgccgatac | 840 | |
| ctgttcctgc acaaccgagg tagatgggac ttcttcttcc atgttgtcat ccagggccgg | 900 | |
| gggacccggc ctgtccttgt ccatttttgtc tgcaacaaaa gtgtgactct ccaacaccgc | 960 | |
| acccccttg tacctattaa agaggatgct gcctagaaat cggtgccgag acaatggagg | 1020 | |
| cagccttgct tgtgtgtcag tacaccatcc agagcctgat ccatctcacg ggtgaagatc | 1080 | |
| ctggttttt caatgttgag attccggaat tcccattta ccccacatgc aatgtttgca | 1140 | |
| cggcagatgt caatgtaact atcaatttcg atgtcgggg caaaaagcat caacttgatc | 1200 | |
| ttgactttgg ccagctgaca ccccatacga aggctgtcta ccaacctcga ggtgcatttg | 1260 | |
| gtggctcaga aaatgccacc aatctctttc tactggagct ccttggtgca ggagaattgg | 1320 | |
| ctctaactat gcggtctaag aagcttccaa ttaacgtcac caccggagag gagcaacaag | 1380 | |
| taagcctgga atctgtagat gtctactttc aagatgtgtt tggaaccatg tggtgccacc | 1440 | |
| atgcagaaat gcaaaacccc gtgtacctga taccagaaac agtgccatac ataaagtggg | 1500 | |
| ataactgtaa ttctaccaat ataacggcag tagtgagggc acaggggctg gatgtcacgc | 1560 | |
| tacccttaag tttgccaacg tcagctcaag actcgaattt cagcgtaaaa acagaaatgc | 1620 | |
| tcggtaatga gatagatatt gagtgtatta tggaggatgg cgaaatttca caagttctgc | 1680 | |
| ccggagacaa caaatttaac atcacctgca gtggatacga gagccatgtt cccagcggcg | 1740 | |
| gaattctcac atcaacgagt cccgtggcca ccccaatacc tggtacaggg tatgcataca | 1800 | |
| gcctgcgtct gacaccacgt ccagtgtcac gatttcttgg caataacagt atcctgtacg | 1860 | |
| tgttttactc tgggaatgga ccgaaggcga gcggggagga ttactgcatt cagtccaaca | 1920 | |
| ttgtgttctc tgatgagatt ccagcttcac aggacatgcc gacaaacacc acagacatca | 1980 | |
| catatgtggg tgacaatgct acctattcag tgccaatggt cacttctgag gacgcaaact | 2040 | |
| cgccaaatgt tacagtgact gccttttggg cctggccaaa caacactgaa actgacttta | 2100 | |
| agtgcaaatg gactctcacc tcggggcacac cttcggttg tgaaaatatt tctggtgcat | 2160 | |
| tgcgagcaa tcggacattt gacattactg tctcgggtct tggcacggcc cccaagacac | 2220 | |
| tcattatcac acgaacggct accaatgcca ccacaacaac ccacaaggtt atattctcca | 2280 | |
| aggcacccga gagcaccacc acctccccta ccttgaatac aactggattt gctgatccca | 2340 | |
| atacaacgac aggtctaccc agctctactc acgtgcctac caacctcacc gcacctgcaa | 2400 | |
| gcacaggccc cactgtatcc accgcggatg tcaccagccc aacaccagcc ggcacaacgt | 2460 | |
| caggcgcatc accggtgaca ccaagtccat ctccatggga caacggcaca gaaagtaagg | 2520 | |

-continued

```
cccccgacat gaccagctcc acctcaccag tgactacccc aaccccaaat gccaccagcc    2580
ccaccccagc agtgactacc ccaaccccaa atgccaccag ccccacccca gcagtgacta    2640
ccccaacccc aaatgccacc agccccacct tgggaaaaac aagtcctacc tcagcagtga    2700 ctacccaac cccaaatgcc accagcccca ccttgggaaa acaagcccc acctcagcag     2760 tgactacccc aaccccaaat gccaccagcc ccaccttggg aaaacaagc cccacctcag    2820 cagtgactac cccaaccca aatgccaccg ccctactgt gggagaaaca agtccacagg     2880
caaatgccac caaccacacc ttaggaggaa caagtcccac cccagtagtt accagccaac    2940
caaaaaatgc aaccagtgct gttaccacag gccaacataa cataacttca agttcaacct    3000
cttccatgtc actgagaccc agttcaaacc cagagacact cagcccctcc accagtgaca    3060
attcaacgtc acatatgcct ttactaacct ccgctcaccc aacaggtggt gaaaatataa    3120
cacaggtgac accagcctct atcagcacac atcatgtgtc caccagttcg ccagaaccc     3180 gcccaggcac caccagccaa gcgtcaggcc ctggaaacag ttccacatcc acaaaaccgg    3240
gggaggttaa tgtcaccaaa ggcacgcccc ccaaaatgc aacgtcgccc caggccccca     3300
gtggccaaaa gacggcggtt cccacggtca cctcaacagg tggaaaggcc aattctacca    3360
ccggtggaaa gcacaccaca ggacatggag cccgacaag tacagagccc accacagatt     3420
acggcggtga ttcaactacg ccaagaccga gatacaatgc gaccacctat ctacctccca    3480
gcacttctag caaactgcgg ccccgctgga cttttacgag cccaccggtt accacagccc    3540
aagccaccgt gccagtcccg ccaacgtccc agcccagatt ctcaaacctc tccatgctag    3600
tactgcagtg ggcctctctg gctgtgctga cccttctgct gctgctggtc atggcggact    3660
gcgcctttag gcgtaacttg tctacatccc atacctacac caccccacca tatgatgacg    3720
ccgagaccta tgtattaaag tcaataaaaa tttattaatc agaatttgca cttctttgc     3780 ttcacgtccc cgggagcggg agcgggcacg tcgggtggcg ttggggtcgt ttgattctcg    3840
tggtcgtgtt ccctcaccag ggctgggttg gccttttgca cccaacatag atacttgaat    3900
gcggagggtc agattttgca atatatttc catttcattg cgggtagtta caccgtcaac     3960
agatttccga accttgtctt caatcttctt catagcctga gacgccaaac ggcccgtggc    4020
ctgcgtaatc attcctctc gctgtcgagc tgtaagcggc tcaggcggag gcactggagc     4080
agaaggaaca gaggtagacg aggcacaggc acccctctg aggacctgtt gcttcagagc     4140
cttattctca gactccaggc gagccaggcg ggcggccatg tcttccatgc tcatgtcaac    4200
agccttaaca gaaggcaatc tgactttgcg tggagctgac atgctattgg tttaacgagc    4260
agagaagaag tacaaacagc cgagattgct gcccctttta aatatcccca tctaatccgt    4320
cagcagcgtg ttcacaaact tgttaaagca gacgtacatc aggtagatgg ctgaggctat    4380
aatgactaag acaagcgtca gaagtgccca gatggaggca aagctggtca agaaggcga    4440 gaatgtgtcc gcattacatg tgtaggagta gaactggtcc tgggcttcag tcagggaagc    4500
cgccgccgcg tttgtgggac tggaagcgcc ggccggcagc accccggtca gaagccaggt    4560
ggcggcgagg aagagcagtg gcacagcctt tgcaacggc tttcttagga ccttccccat     4620
ttcgcagtaa agagagccgg gtcttgggct cttatatata gcgccgccgt ccctgtctgt    4680
tagatcatca ccatggaggc ctgtccacac atacgctacg ccttccagaa tgacaagctg    4740
ttgctccagc aggagctcaa aatccacctg gctgccttca gatatgccac ccccctgctg    4800
cgcccgatga agaccacaac tgtggaccta ggcctctatg cccgcccacc cgagggtcat    4860
```

-continued

```
gggctcatgc tgtggggcag cacctcccgt ccggtcacgt ctcatgttgg catcatcgat    4920
cccggctaca cggggggaact ccggctaatc ctccagaatc agcggcgcta caactccacg   4980
ctgcgtccat cggagctcaa aatccacctg gctgccttca gatatgccac cccccagatg   5040
gaggaggaca agggtcccat caaccacccc cagtaccccg gggacgtggg cctggacgtc   5100
tctttgccaa aggacctggc cctcttcccc catcagaccg tctcagtgac actcaccgtg   5160 ccccccccctt ctatccctca ccacaggccg acaatctttg gcaggtcggg cctggccatg   5220
cagggtattc tagtgaagcc ctgcaggtgg cgccggggtg gggtggacgt cagcctgacc   5280
aactttagtg accagaccgt gttccttaac aagtaccggc gcttctgtca gcttgtttac   5340
cttcacaagc accactcac ctccttctac agcccccaca gtgacgcggg ggtccttggc    5400
cccagatctc tctttaggtg ggccagctgc accttcgagg aggtgccgag cctggccatg   5460
ggtgatagtg ggctgagcga ggcgctcgag gggagacagg ggaggggggtt tggatcctcg   5520 ggtcaatgac accttcatat cccttgtttt accaataaaa tgtttatttg gtgtggagtc   5580
tggttgctac gttaacgcga gctccgtggg cccagagtgc tccggctgcc gcaccacggg   5640
aggcggtgca aggacggggg tgggcacctc gggctcaaag gcggagttga tgaaaggggc   5700
cgaggctgag ggggcggtca ccgatgagac aacggccgag atctcttgcg cccaggcacc   5760
ggtctcgtcc atcttgagcg ccgtggccac cttctccatc tccatcaggg ccaggctgtc   5820
gccagcctgt ttgtccagca gggccttgag cccattctcg tccatctcga tgccgcttac   5880
agccagagag atcatggtat tccagatgac tgagcgcacg gcctcaagct t            5931
```

<210> SEQ ID NO 2
<211> LENGTH: 878
<212> TYPE: PRT
<213> ORGANISM: Virus
<220> FEATURE:
<223> OTHER INFORMATION: gp350

<400> SEQUENCE: 2

```
Met Glu Ala Ala Leu Leu Val Cys Gln Tyr Thr Ile Gln Ser Leu Ile
1               5                   10                  15

His Leu Thr Gly Glu Asp Pro Gly Phe Phe Asn Val Glu Ile Pro Glu
            20                  25                  30

Phe Pro Phe Tyr Pro Thr Cys Asn Val Cys Thr Ala Asp Val Asn Val
        35                  40                  45

Thr Ile Asn Phe Asp Val Gly Gly Lys Lys His Gln Leu Asp Leu Asp
    50                  55                  60

Phe Gly Gln Leu Thr Pro His Thr Lys Ala Val Tyr Gln Pro Arg Gly
65                  70                  75                  80

Ala Phe Gly Gly Ser Glu Asn Ala Thr Asn Leu Phe Leu Leu Glu Leu
                85                  90                  95

Leu Gly Ala Gly Glu Leu Ala Leu Thr Met Arg Ser Lys Lys Leu Pro
            100                 105                 110

Ile Asn Val Thr Thr Gly Glu Glu Gln Gln Val Ser Leu Glu Ser Val
        115                 120                 125

Asp Val Tyr Phe Gln Asp Val Phe Gly Thr Met Trp Cys His His Ala
    130                 135                 140

Glu Met Gln Asn Pro Val Tyr Leu Ile Pro Glu Thr Val Pro Tyr Ile
145                 150                 155                 160

Lys Trp Asp Asn Cys Asn Ser Thr Asn Ile Thr Ala Val Val Arg Ala
                165                 170                 175
```

```
Gln Gly Leu Asp Val Thr Leu Pro Leu Ser Leu Pro Thr Ser Ala Gln
            180                 185                 190

Asp Ser Asn Phe Ser Val Lys Thr Glu Met Leu Gly Asn Glu Ile Asp
            195                 200                 205

Ile Glu Cys Ile Met Glu Asp Gly Glu Ile Ser Gln Val Leu Pro Gly
            210                 215                 220

Asp Asn Lys Phe Asn Ile Thr Cys Ser Gly Tyr Glu Ser His Val Pro
225                 230                 235                 240

Ser Gly Gly Ile Leu Thr Ser Thr Ser Pro Val Ala Thr Pro Ile Pro
            245                 250                 255

Gly Thr Gly Tyr Ala Tyr Ser Leu Arg Leu Thr Pro Arg Pro Val Ser
            260                 265                 270

Arg Phe Leu Gly Asn Asn Ser Ile Leu Tyr Val Phe Tyr Ser Gly Asn
            275                 280                 285

Gly Pro Lys Ala Ser Gly Gly Asp Tyr Cys Ile Gln Ser Asn Ile Val
            290                 295                 300

Phe Ser Asp Glu Ile Pro Ala Ser Gln Asp Met Pro Thr Asn Thr Thr
305                 310                 315                 320

Asp Ile Thr Tyr Val Gly Asp Asn Ala Thr Tyr Ser Val Pro Met Val
            325                 330                 335

Thr Ser Glu Asp Ala Asn Ser Pro Asn Val Thr Val Thr Ala Phe Trp
            340                 345                 350

Ala Trp Pro Asn Asn Thr Glu Thr Asp Phe Lys Cys Lys Trp Thr Leu
            355                 360                 365

Thr Ser Gly Thr Pro Ser Gly Cys Glu Asn Ile Ser Gly Ala Phe Ala
            370                 375                 380

Ser Asn Arg Thr Phe Asp Ile Thr Val Ser Gly Leu Gly Thr Ala Pro
385                 390                 395                 400

Lys Thr Leu Ile Ile Thr Arg Thr Ala Thr Asn Ala Thr Thr Thr Thr
            405                 410                 415

His Lys Val Ile Phe Ser Lys Ala Pro Glu Ser Thr Thr Ser Pro
            420                 425                 430

Thr Leu Asn Thr Thr Gly Phe Ala Asp Pro Asn Thr Thr Gly Leu
            435                 440                 445

Pro Ser Ser Thr His Val Pro Thr Asn Leu Thr Ala Pro Ala Ser Thr
            450                 455                 460

Gly Pro Thr Val Ser Thr Ala Asp Val Thr Ser Pro Thr Pro Ala Gly
465                 470                 475                 480

Thr Thr Ser Gly Ala Ser Pro Val Thr Pro Ser Pro Ser Pro Trp Asp
            485                 490                 495

Asn Gly Thr Glu Ser Lys Ala Pro Asp Met Thr Ser Ser Thr Ser Pro
            500                 505                 510

Val Thr Thr Pro Thr Pro Asn Ala Thr Ser Pro Thr Pro Ala Val Thr
            515                 520                 525

Thr Pro Thr Pro Asn Ala Thr Ser Pro Thr Pro Ala Val Thr Pro
            530                 535                 540

Thr Pro Asn Ala Thr Ser Pro Thr Leu Gly Lys Thr Ser Pro Thr Ser
545                 550                 555                 560

Ala Val Thr Thr Pro Thr Pro Asn Ala Thr Ser Pro Thr Leu Gly Lys
            565                 570                 575

Thr Ser Pro Thr Ser Ala Val Thr Thr Pro Thr Pro Asn Ala Thr Ser
            580                 585                 590

Pro Thr Leu Gly Lys Thr Ser Pro Thr Ser Ala Val Thr Thr Pro Thr
```

```
                595                 600                 605
Pro Asn Ala Thr Gly Pro Thr Val Gly Glu Thr Ser Pro Gln Ala Asn
            610                 615                 620
Ala Thr Asn His Thr Leu Gly Gly Thr Ser Pro Thr Pro Val Val Thr
625                 630                 635                 640
Ser Gln Pro Lys Asn Ala Thr Ser Ala Val Thr Thr Gly Gln His Asn
                645                 650                 655
Arg Pro Ser Ser Asn Pro Glu Thr Leu Ser Pro Ser Thr Ser Asp Asn
            660                 665                 670
Ser Thr Ser His Met Gly Gly Glu Asn Ile Thr Gln Val Thr Pro Ala
        675                 680                 685
Ser Ile Ser Thr His His Val Ser Thr Ser Ser Pro Glu Pro Arg Pro
        690                 695                 700
Gly Thr Thr Ser Gln Ala Ser Gly Pro Gly Asn Ser Ser Thr Ser Thr
705                 710                 715                 720
Lys Pro Gly Glu Val Asn Val Thr Lys Gly Thr Pro Pro Gln Asn Ala
                725                 730                 735
Thr Ser Pro Gln Ala Pro Ser Gly Gln Lys Thr Ala Val Pro Thr Val
            740                 745                 750
Thr Ser Thr Gly Gly Lys Ala Asn Ser Thr Thr Gly Gly Lys His Thr
        755                 760                 765
Thr Gly His Gly Ala Arg Thr Ser Thr Glu Pro Thr Thr Asp Tyr Gly
        770                 775                 780
Gly Asp Ser Thr Thr Pro Arg Pro Arg Tyr Asn Ala Thr Thr Tyr Leu
785                 790                 795                 800
Pro Pro Ser Thr Ser Ser Lys Leu Arg Pro Arg Trp Thr Phe Thr Ser
                805                 810                 815
Pro Pro Val Thr Thr Ala Gln Ala Thr Val Pro Val Pro Pro Thr Ser
            820                 825                 830
Gln Pro Arg Phe Ser Asn Leu Ser Met Leu Val Leu Leu Leu Leu Leu
            835                 840                 845
Leu Val Met Ala Asp Cys Ala Phe Arg Arg Asn Leu Ser Thr Ser His
        850                 855                 860
Thr Tyr Thr Thr Pro Pro Tyr Asp Asp Ala Glu Thr Tyr Val
865                 870                 875

<210> SEQ ID NO 3
<211> LENGTH: 27
<212> TYPE: DNA
<213> ORGANISM: Artificial Sequence
<220> FEATURE:
<223> OTHER INFORMATION: primer

<400> SEQUENCE: 3
ggatcctaga ctgcgccttt aggcgta                                      27

<210> SEQ ID NO 4
<211> LENGTH: 19
<212> TYPE: DNA
<213> ORGANISM: Artificial Sequence
<220> FEATURE:
<223> OTHER INFORMATION: primer

<400> SEQUENCE: 4
gactgcgcct ttaggcgta                                               19

<210> SEQ ID NO 5
```

```
<211> LENGTH: 6
<212> TYPE: PRT
<213> ORGANISM: Artificial Sequence
<220> FEATURE:
<223> OTHER INFORMATION: peptide

<400> SEQUENCE: 5

Asp Cys Ala Phe Arg Arg
1               5

<210> SEQ ID NO 6
<211> LENGTH: 27
<212> TYPE: DNA
<213> ORGANISM: Artificial Sequence
<220> FEATURE:
<223> OTHER INFORMATION: primer

<400> SEQUENCE: 6
ggatcctctg ttccttctgc tccagtg                                   27

<210> SEQ ID NO 7
<211> LENGTH: 21
<212> TYPE: DNA
<213> ORGANISM: Artificial Sequence
<220> FEATURE:
<223> OTHER INFORMATION: primer

<400> SEQUENCE: 7
tctgttcctt ctgctccagt g                                         21

<210> SEQ ID NO 8
<211> LENGTH: 16
<212> TYPE: DNA
<213> ORGANISM: Artificial Sequence
<220> FEATURE:
<223> OTHER INFORMATION: primer

<400> SEQUENCE: 8
tatagactag tctagg                                               16

<210> SEQ ID NO 9
<211> LENGTH: 18
<212> TYPE: DNA
<213> ORGANISM: Artificial Sequence
<220> FEATURE:
<223> OTHER INFORMATION: primer

<400> SEQUENCE: 9
atctgatcag atccttaa                                             18

<210> SEQ ID NO 10
<211> LENGTH: 39
<212> TYPE: DNA
<213> ORGANISM: Artificial Sequence
<220> FEATURE:
<223> OTHER INFORMATION: primer

<400> SEQUENCE: 10
ccgcgtcagg cggtactggt catgatcgta cctctccaa                      39

<210> SEQ ID NO 11
<211> LENGTH: 13
<212> TYPE: PRT
<213> ORGANISM: Virus

<400> SEQUENCE: 11
```

```
Ala Cys Asp Ala Met Val Leu Val Leu Met Ser Leu Asn
1               5                   10
```

<210> SEQ ID NO 12
<211> LENGTH: 30
<212> TYPE: DNA
<213> ORGANISM: Virus

<400> SEQUENCE: 12
ggatcttgat cagatatcgt acctctccaa                                           30

<210> SEQ ID NO 13
<211> LENGTH: 5
<212> TYPE: PRT
<213> ORGANISM: Artificial Sequence
<220> FEATURE:
<223> OTHER INFORMATION: peptide

<400> SEQUENCE: 13

```
Leu Met Ser Leu Asn
1               5
```

<210> SEQ ID NO 14
<211> LENGTH: 24
<212> TYPE: DNA
<213> ORGANISM: Artificial Sequence
<220> FEATURE:
<223> OTHER INFORMATION: primer

<400> SEQUENCE: 14
ccgcgtcaga tcgtacctct ccaa                                                 24

<210> SEQ ID NO 15
<211> LENGTH: 8
<212> TYPE: PRT
<213> ORGANISM: Artificial Sequence
<220> FEATURE:
<223> OTHER INFORMATION: peptide

<400> SEQUENCE: 15

```
Ala Cys Asp Leu Met Ser Leu Asn
1               5
```

<210> SEQ ID NO 16
<211> LENGTH: 42
<212> TYPE: DNA
<213> ORGANISM: Artificial Sequence
<220> FEATURE:
<223> OTHER INFORMATION: Mutagenesis oligonucleotide as PrDonor1

<400> SEQUENCE: 16
ggtcatgtcg ggggcctttg actctgtgcc gttgtcccat gg                             42

<210> SEQ ID NO 17
<211> LENGTH: 42
<212> TYPE: DNA
<213> ORGANISM: Virus

<400> SEQUENCE: 17
ggtcatgtcg ggggccttac tttctgtgcc gttgtcccat gg                             42

<210> SEQ ID NO 18
<211> LENGTH: 42
<212> TYPE: DNA
<213> ORGANISM: Artificial Sequence
<220> FEATURE:

-continued

```
<223> OTHER INFORMATION: Mutagenesis oligonucleotide as PrAcceptor1

<400> SEQUENCE: 18
ctgtgttata ttttcacctc cagttgggtg agcggaggtt ag                    42

<210> SEQ ID NO 19
<211> LENGTH: 42
<212> TYPE: DNA
<213> ORGANISM: Virus

<400> SEQUENCE: 19
ctgtgttata ttttcaccac ctgttgggtg agcggaggtt ag                    42
```